United States Patent
Shetty et al.

(10) Patent No.: US 10,328,211 B2
(45) Date of Patent: Jun. 25, 2019

(54) AUTOMATIC SELF-DISPENSING ACCURATE DOSE DRUG DELIVERY SYRINGES

(71) Applicant: UNL Holdings LLC, New York, NY (US)

(72) Inventors: Gautam N. Shetty, Lancaster, PA (US); Lou Castagna, Middletown, PA (US)

(73) Assignee: UNL Holdings LLC, New York, NY (US)

( * ) Notice: Subject to any disclaimer, the term of this patent is extended or adjusted under 35 U.S.C. 154(b) by 270 days.

(21) Appl. No.: 15/021,622

(22) PCT Filed: Sep. 12, 2014

(86) PCT No.: PCT/US2014/055486
§ 371 (c)(1),
(2) Date: Mar. 11, 2016

(87) PCT Pub. No.: WO2015/047758
PCT Pub. Date: Apr. 2, 2015

(65) Prior Publication Data
US 2016/0220761 A1    Aug. 4, 2016

Related U.S. Application Data

(63) Continuation-in-part of application No. 13/707,201, filed on Dec. 6, 2012, now Pat. No. 9,345,839.
(Continued)

(51) Int. Cl.
*A61M 5/315* (2006.01)
*A61M 5/20* (2006.01)
(Continued)

(52) U.S. Cl.
CPC .......... *A61M 5/31551* (2013.01); *A61M 5/20* (2013.01); *A61M 5/2033* (2013.01);
(Continued)

(58) Field of Classification Search
CPC .. A61M 5/20; A61M 5/2033; A61M 5/31526; A61M 5/31528; A61M 5/31551
See application file for complete search history.

(56) References Cited

U.S. PATENT DOCUMENTS 2,565,081 A    8/1951 Maynes
2,943,624 A    7/1960 Alquist
(Continued)

FOREIGN PATENT DOCUMENTS

EP        1932558 A1    6/2008
WO    WO 02/053214 A1    7/2002
(Continued)

OTHER PUBLICATIONS

European Patent Office, International Search Report and Written Opinion from International Application No. PCT/US2014/055486 (dated Jun. 10 2015) 18 pgs.

*Primary Examiner* — Deanna K Hall
(74) *Attorney, Agent, or Firm* — Hamilton, Brook, Smith & Reynolds, P.C.

(57) ABSTRACT

An automatic accurate dose syringe includes a barrel, a plunger seal, a barrel adapter assembly having a barrel tip and a needle, and a dose control mechanism having a plunger having a coarse pitch screw on its exterior surface, a housing having a corresponding coarse pitch guide along the interior surface of the housing, a screw having a fine pitch screw which interfaces with a fine pitch nut of an adapter, wherein the plunger has an internal annular space within which screw at least partially resides. The syringe further includes a locking mechanism, an activation button, and a biasing member such as a compression and/or a torsional spring. The components are configured such that actuation of the activation button by the user manipulates the locking mechanism to permit the biasing member to move (Continued)

from an initial energized state to a lower energy state, thereby automating drug delivery from the syringe.

11 Claims, 12 Drawing Sheets

Related U.S. Application Data

(60) Provisional application No. 62/005,089, filed on May 30, 2014, provisional application No. 61/877,723, filed on Sep. 13, 2013, provisional application No. 61/568,509, filed on Dec. 8, 2011.

(51) Int. Cl.
 *A61M 5/28* (2006.01)
 *A61M 5/36* (2006.01)
 *A61M 5/31* (2006.01)

(52) U.S. Cl.
 CPC .......... *A61M 5/28* (2013.01); *A61M 5/31526* (2013.01); *A61M 5/31528* (2013.01); *A61M 5/31575* (2013.01); *A61M 5/3146* (2013.01); *A61M 5/36* (2013.01); *A61M 2005/3139* (2013.01); *A61M 2005/3152* (2013.01); *A61M 2205/80* (2013.01); *Y10T 29/49826* (2015.01)

(56) References Cited

U.S. PATENT DOCUMENTS

| | | |
|---|---|---|
| 3,596,659 A | 8/1971 | Glasser |
| 4,018,223 A | 4/1977 | Ethington |
| 4,444,335 A | 4/1984 | Wood et al. |
| 4,465,478 A | 8/1984 | Sabelman et al. |
| 4,687,472 A | 8/1987 | Gross |
| 4,865,591 A | 9/1989 | Sams |
| 4,936,833 A | 6/1990 | Sams |
| 5,104,380 A | 4/1992 | Holman et al. |
| 5,115,816 A | 5/1992 | Lee |
| 5,135,511 A | 8/1992 | Houghton et al. |
| 5,250,030 A | 10/1993 | Corsich |
| 5,346,475 A | 9/1994 | Gregorio |
| 5,378,233 A | 1/1995 | Haber et al. |
| 5,531,691 A | 7/1996 | Shonfeld et al. |
| 5,562,623 A | 10/1996 | Shonfeld et al. |
| 5,582,595 A | 12/1996 | Haber et al. |
| 5,819,983 A | 10/1998 | White et al. |
| 5,971,227 A | 10/1999 | White et al. |
| 6,231,550 B1 | 5/2001 | Laughlin |
| 6,283,941 B1 | 9/2001 | Schoenfeld et al. |
| 6,533,756 B2 | 3/2003 | Schoenfeld et al. |
| 6,719,735 B1 | 4/2004 | Gammon |
| 6,957,752 B2 | 10/2005 | Py et al. |
| 7,290,573 B2 | 11/2007 | Py et al. |
| 7,500,959 B2 | 3/2009 | Munk |
| 7,611,495 B1 | 11/2009 | Gianturco |
| 7,798,185 B2 | 9/2010 | Py et al. |
| 7,857,791 B2 | 12/2010 | Jacobs et al. |
| 7,867,202 B2 | 1/2011 | Moser et al. |
| 7,959,609 B2 | 6/2011 | Gaydos et al. |
| 7,967,772 B2 | 6/2011 | McKenzie et al. |
| 8,057,427 B2 | 11/2011 | Griffiths et al. |
| 2003/0004467 A1 | 1/2003 | Musick et al. |
| 2005/0215958 A1 | 9/2005 | Hawthorne |
| 2008/0243087 A1* | 10/2008 | Enggaard .......... A61M 5/31553 604/208 |
| 2009/0275914 A1 | 11/2009 | Harms et al. |
| 2010/0305512 A1 | 12/2010 | Guillermo et al. |
| 2010/0331808 A1 | 12/2010 | Py et al. |

FOREIGN PATENT DOCUMENTS

| | | |
|---|---|---|
| WO | WO 2006/108243 A2 | 10/2006 |
| WO | WO 2010/063687 A1 | 6/2010 |

* cited by examiner

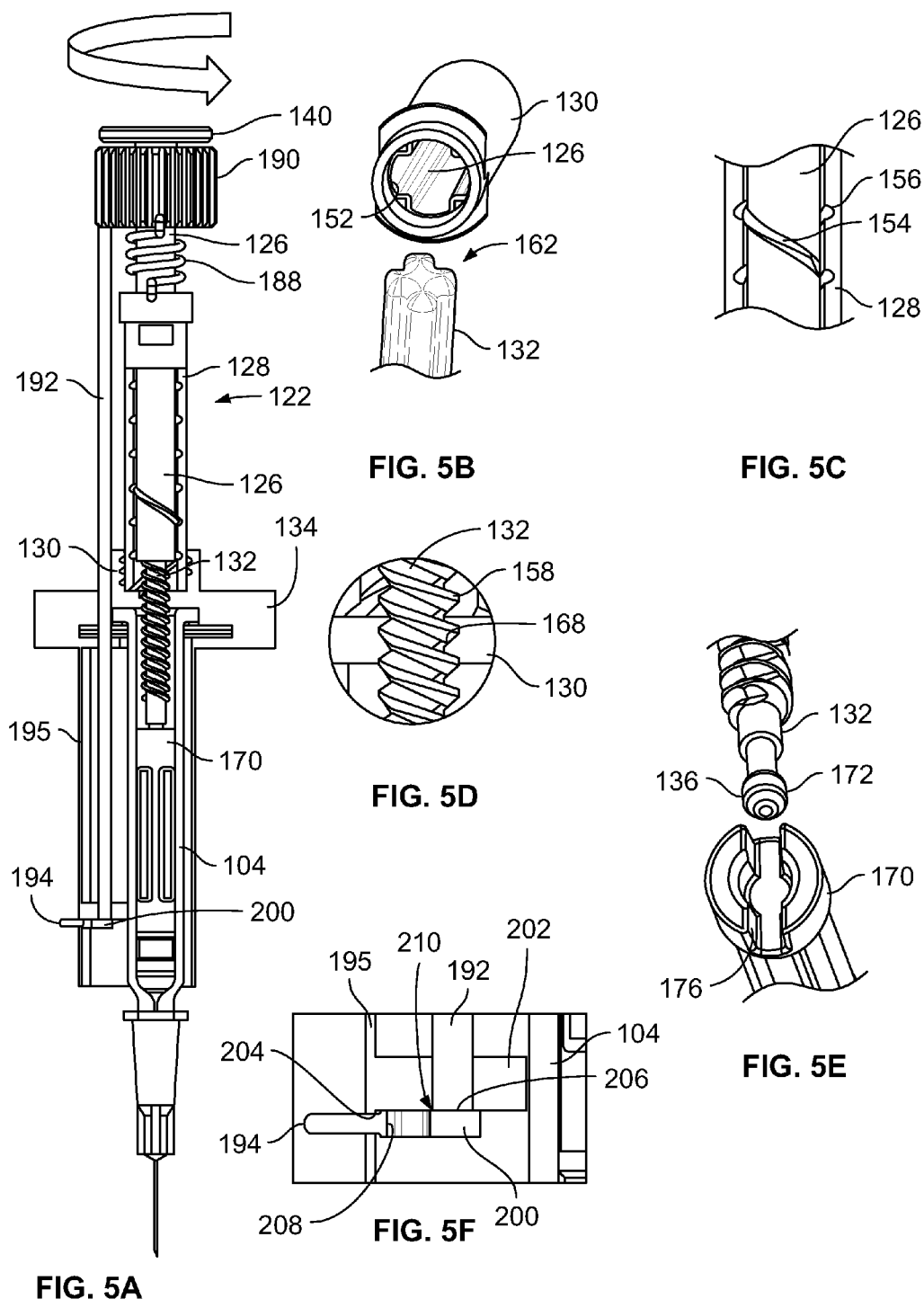

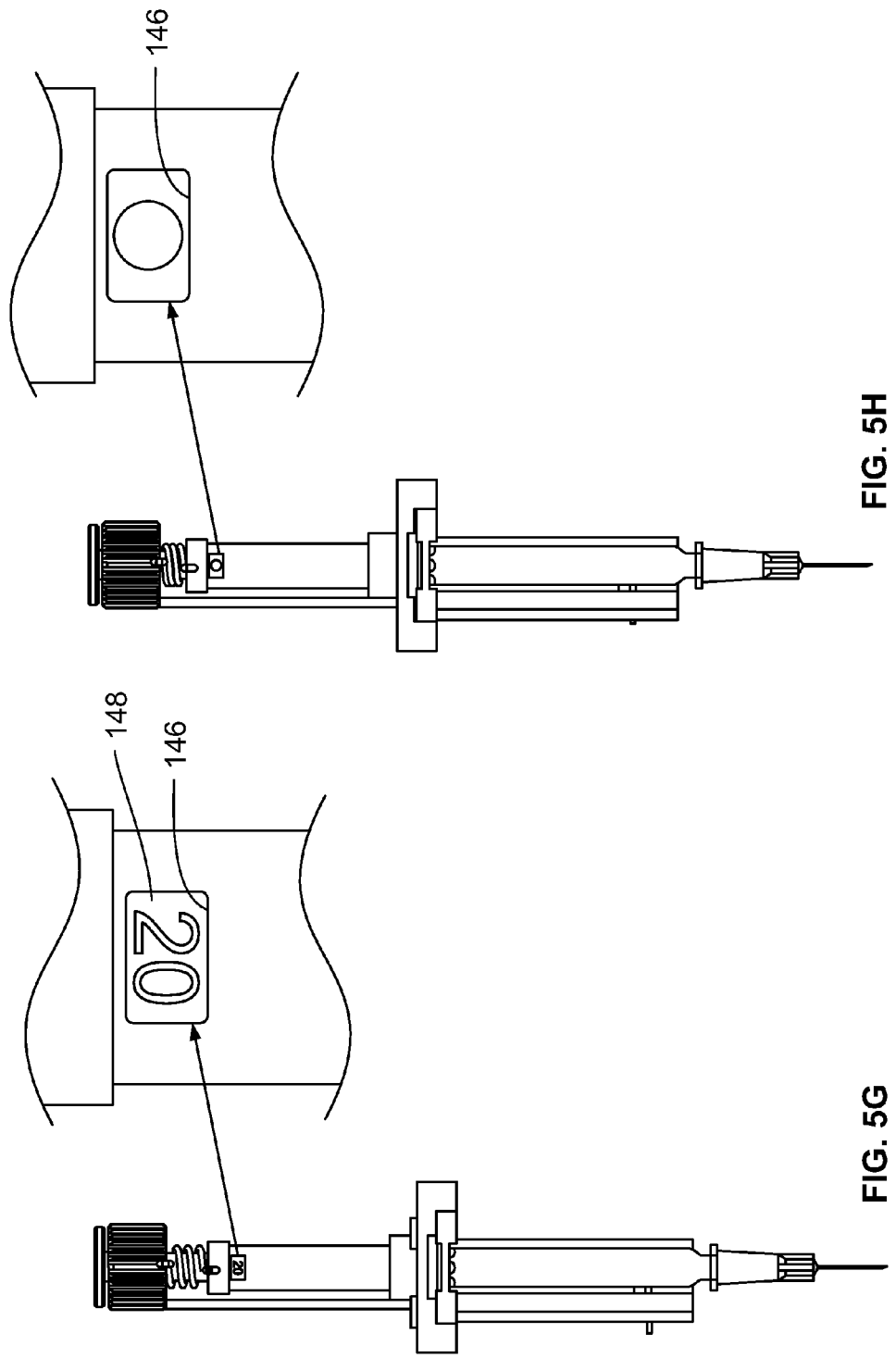

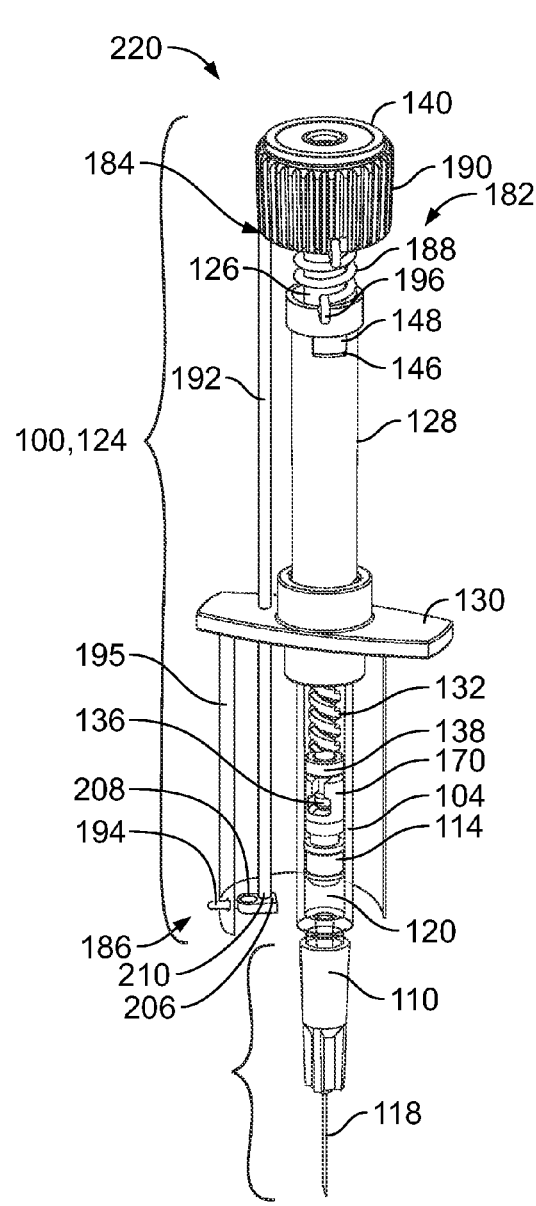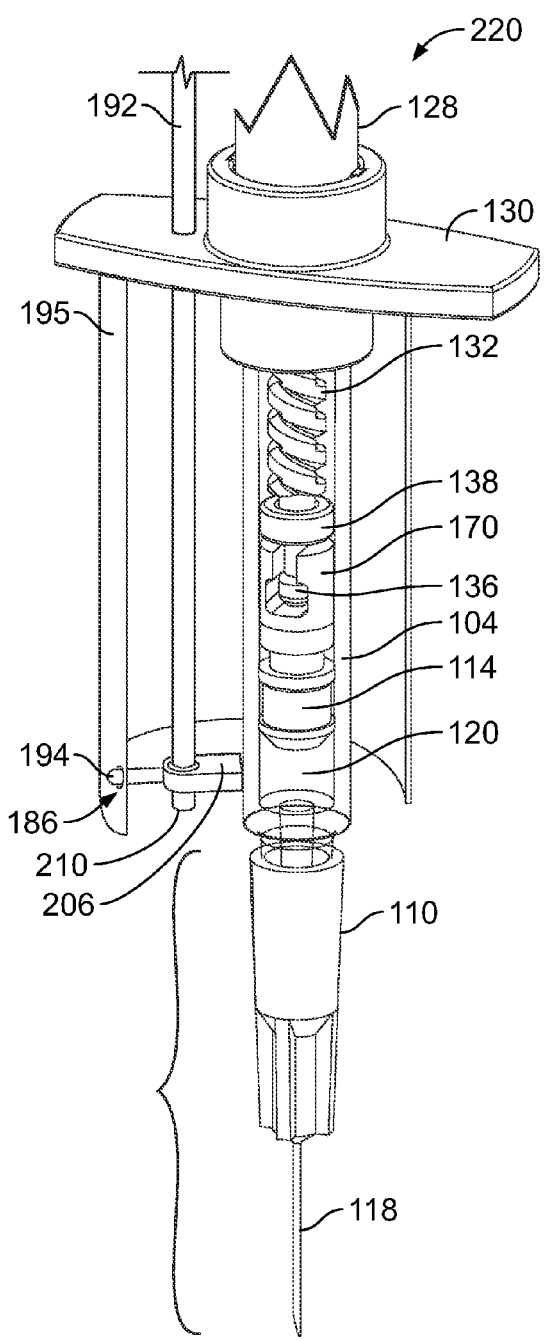
FIG. 6A                    FIG. 6B

AUTOMATIC SELF-DISPENSING ACCURATE DOSE DRUG DELIVERY SYRINGES

CROSS-REFERENCE TO RELATED APPLICATIONS

This application is a national phase application of International Patent Application No. PCT/US2014/055486, filed Sep. 12, 2014, which claims priority to U.S. Provisional Application No. 61/877,723 filed Sep. 13, 2013, and U.S. Provisional Application No. 62/005,089 filed May 30, 2014, each of which is included by reference herein in their entireties for all purposes. This application is also a continuation-in-part of U.S. application Ser. No. 13/707,201 filed Dec. 6, 2012, which claims priority to U.S. Provisional Application No. 61/568,509 filed Dec. 8, 2011 , each of which is incorporated by reference in its entirety for all purposes.

FIELD

THIS INVENTION relates to accurate dose drug delivery syringes. More particularly, this invention relates to automatic accurate dose drug delivery syringes which are capable of self-dispensing upon activation by a user, the methods of operating such devices, and the methods of assembling such devices.

BACKGROUND

Various studies have shown that the accuracy of dose delivery is affected by a number of factors, including: injection methodologies employed by medical practitioners, an inability to accurately read and control plunger travel during dosing, and the loss of dosage associated with the prime step used to evacuate air from the syringe prior to the dosing step. These effects are particularly magnified by the use of drug delivery syringes that have a high dose volume to axial translation ratio (i.e., a significant quantity of drug is dispensed for even incrementally small distances of plunger depression, as may be the case for large diameter syringes); this problem is more acute when delivering microliter size doses. While these causes for error are common, the need for accurate dose syringes remains. Such syringes are of particular importance in sensitive operations, such as in intravitreal injections, and are very desirable for low dose treatments where inaccurate dosing can lead to substantial error and potential patient harm.

Studies have shown that the amount of treatment delivered may vary significantly depending on whether the medical practitioner chooses to deliver 5 µL (5 microliters) of the treatment by depressing the syringe plunger from 10 µL to 5 µL or by depressing the syringe from 5 µL to 0 µL. Additionally, due to the uncertainty of plunger travel limits some practitioners may depress the syringe past the natural travel limit and deliver excess treatment to the patient because of mechanical compliance between the stopper and the syringe barrel. For example, given a particular syringe barrel diameter, a practitioner may depress the plunger past the natural stop for 0 µL and erroneously deliver up to 20% more dosage than necessary. This error is magnified because of the small dose volume requirements for particular treatments. Because the dosage amount and associated plunger travel distance are small, it is very difficult for a practitioner to gauge the fill amount of the dosing chamber and to control the injection amount as the treatment is applied to the patient. This inaccuracy in dosing can lead to substantial safety risks including, among other side effects, increased pressure in the target region and altered (reduced) drug efficacy.

A primary cause of the dosing inaccuracy is the inability to reliably set the limits of plunger travel, and the inherent variability in the degree to which the plunger seal (or stopper) is depressed at end of delivery during dosing. Also contributing to inaccuracy is the potential variability, during syringe manufacturing, in the placement of reference markings on the syringe barrel. Endemic to these causes of inaccuracy is the high sensitivity of volume dispensed to the axial travel of the plunger, as described above. Mechanical travel limits, however, are difficult to employ in such applications because of the challenges associated with reading and controlling the plunger travel by the user over the small distance of dosing. Simply put, because the dosage amounts are so small, it is difficult for a practitioner to identify the dosage measurements on the syringe barrel and accurately control the plunger depression and dosage amount during injection.

In addition to improving dosing accuracy, it is useful to incorporate the functionality of a priming step into a syringe design to reduce or eliminate air bubbles within the dosing chamber. This step is very useful to minimize safety risks, improve operational hygiene, and reduce pressure in the target site. Minimizing the likelihood of air bubbles during filling helps streamline the drug delivery process for the clinician. Employing pre-filled syringes may assist in the minimization of air bubbles. However, even pre-filled syringes are not fully devoid of air captured during the filling process.

Accordingly, there is a substantial need for syringes which allow the user to readily identify and control the dosage amount, minimize the presence of air bubbles within the dosage chamber prior to drug delivery, and ensure accurate delivery of the required drug dose. It is preferred that such a syringe would enable pre-filling to take advantage of benefits associated with the use of such products.

Various syringes have been developed in attempts to address dosing inaccuracies in drug administration. For example, U.S. Application Publication 2013/0150803 A1 to Shetty et al., which is assigned to the assignee of this disclosure, discloses a syringe having a plunger rod that is externally threaded with a course pitch to a housing. A screw that engages a plunger seal is keyed to the plunger rod, and externally threaded with a fine pitch to an adapter secured to the housing. While the differences between the pitches enhance dosing accuracy, operation of the syringe is still dependent upon and subject to variability of manual administration.

SUMMARY

The present invention provides dose control mechanisms, which may allow for the accurate dosing and delivery of drug treatments, and drug delivery syringes which incorporate such control mechanisms. Such novel devices may permit the identification and control of the dosage amount, permit the syringe to be "primed" (i.e., evacuated of air bubbles) prior to drug delivery, and ensure the accurate delivery of microliter volume dosages, all within a device size that is similar to commonly used conventional syringes available in the marketplace. Such novel devices are generally safe and easy to use, and are aesthetically and ergonomically appealing for clinical practitioners. The novel devices of the present invention may provide these desirable features while minimizing problems associated with known prior art devices.

In accordance with an aspect of this disclosure, there is provided an automated dose control mechanism for a syringe that has a barrel and a plunger seal. The dose control mechanism includes a plunger assembly and an automatic administration assembly. The plunger assembly is adapted to be connected to the syringe to provide movement to the plunger seal. The automatic administration assembly includes an administration mechanism, a locking mechanism, and an actuator. The administration mechanism is adapted and disposed to provide selective movement to the plunger assembly. The locking mechanism is adapted to be disposed in an engaged position to prevent the administration mechanism from providing movement to the plunger assembly, and a disengaged position wherein the locking mechanism does not prevent the administration mechanism from providing movement to the plunger assembly. The actuator is disposed to selectively engage and disengage the locking mechanism with the administration mechanism. When actuator is disposed to engage the locking mechanism, the locking mechanism prevents the administration mechanism from providing administration movement to the plunger assembly. Conversely, the administration mechanism provides administration movement to the plunger assembly when the locking mechanism is disengaged without requiring further actuation.

According to another aspect of some embodiments, the administration mechanism can include a biasing element and a selection dial. Alternately, the administration mechanism can include a motor or any other appropriate arrangement that provides automatic movement of the plunger assembly once actuated. According another aspect of some embodiments, the locking mechanism may include a locking pin or other surface that engages or abuts a component of the administration mechanism. According to yet another aspect of some embodiments, the actuator may include a dispense button that selectively allows the locking mechanism to disengage the administration mechanism. Some embodiments may include a voice activated arrangement or a remotely actuated arrangement, such as a foot pedal.

In accordance with a first embodiment, there is provided an accurate dose drug delivery syringe having a dose control mechanism, a barrel, a plunger seal, and a barrel adapter assembly having a barrel tip and a needle. The control mechanism includes a plunger having a coarse pitch screw on its exterior surface, a housing having a corresponding coarse pitch guide along the interior surface of the housing, a screw having a fine pitch screw which interfaces with a fine pitch nut of an adapter, wherein the plunger has an internal annular space within which screw at least partially resides. The syringe may further include a plunger rod connected at one end to screw and at another end to plunger seal. The plunger having the coarse pitch is rotatable upon the corresponding coarse pitch guide, and wherein at least a portion of the plunger is rotationally keyed to interface with a corresponding rotationally keyed portion of screw. A pitch ratio between the coarse pitch screw and the fine pitch screw may be from approximately 1:1 to approximately 20:1, more specifically from approximately 2:1 to approximately 10:1, and more preferably from approximately 4:1 to approximately 8:1. In a currently preferred embodiment, the pitch ratio of the coarse pitch screw and the fine pitch screw is approximately 4:1.

The screw may further include a screw connection aspect and, optionally, a ring which function to connect the screw to the plunger seal directly or to a plunger rod. In at least one embodiment, the housing has a housing cover at its proximal end and a window to permit the user to view the location of the plunger within housing. The plunger may have one or more dose markings on the external surface of the plunger and the housing may have one or more guide markings with which to align plunger dose markings. Upon use by the user, plunger axially translates a first distance D1 causing screw to axially translate a second distance D2, wherein D1 is always greater than D2 by a factor determined by the pitch ratio. The syringe may be a fill-at-time-of-use syringe, a pre-filled syringe, or a safety syringe, or a combination thereof. The housing of the syringe may have a housing cover at its proximal end to protect the interior of the housing from the environment and a window to permit the user to view the location of the plunger within housing.

In a currently preferred embodiment, the syringe further includes a locking mechanism, an activation button, and a biasing member. The biasing member may be a spring, such as a compression spring and/or a torsional spring. The activation button, biasing member, and locking mechanism are configured such that actuation of the activation button by the user manipulates the locking mechanism to permit the biasing member to move from an initial energized state to a lower energy or deenergized state. In one embodiment, when the activation button is depressed, a locking pin of the locking mechanism is manipulated to release the plunger of the syringe. The biasing member is then permitted to act on the plunger, causing it to axially translate and axially rotate, as described further herein. Torque may be transferred from the plunger to the coarse pitch screw, the fine pitch screw, and through the keyed interface of the fine pitch nut, thereby transferring force to the plunger rod. The plunger rod preferably only axially translates, i.e. the plunger rod does not axially rotate, due to the slip fit with the screw. The plunger seal is caused to translate as it is connected or adjacent to the plunger rod, thereby delivering a drug or therapy to a user through a needle or cannula. When a torsional spring, or a torsional compression spring, is utilized as the biasing member, the torque of the spring is thus utilized to translate the plunger seal for drug delivery. In a preferred embodiment, these components may be configured to operate with the dose control mechanisms as described in International Publication WO2013/086167, although without limitation thereto.

In an alternative currently preferred embodiment, the biasing member may be an electrical, mechanical, or electromechanical component that, for example, acts on the plunger, causing it to axially translate and axially rotate, as described further herein. Torque may be transferred from the plunger to the coarse pitch screw, the fine pitch screw, and through the keyed interface of the fine pitch nut, thereby transferring force to the plunger rod. The plunger rod in at least one embodiment only axially translates, i.e. the plunger rod does not axially rotate, due to the slip fit with the screw. The plunger seal is caused to translate as it is connected or adjacent to the plunger rod, thereby delivering a drug or therapy to a user through a needle or cannula. When an electrical, mechanical, or electromechanical component is utilized as the biasing member, the torque of such component may be utilized to translate the plunger seal for drug delivery. In a particular embodiment, an electromechanical biasing member, such as a motor, is employed to cause axial translation and axial rotation of the plunger. The motor, such as a stepper motor, may be controlled by a myriad of mechanisms or methodologies. For example, the motor, biasing member, and/or plunger may be controlled by a foot-operated actuation mechanism, a voice-activated actuation mechanism, or other such control or actuation mechanism. In at least one particular embodiment, the biasing member is controlled by a foot-operated actuation mechanism. In another particular embodiment, the biasing member is controlled by a voice-activated actuation mechanism. In a preferred embodiment, these components may be configured to operate with the dose control mechanisms as described in International Publication WO2013/086167, although without limitation thereto.

In a further embodiment, a method of manufacturing a syringe having a control mechanism includes the steps of: (i) mounting a barrel adapter assembly to a distal end of a syringe barrel; (ii) mounting a plunger seal through a proximal end of the syringe barrel; and (iii) mounting a control mechanism to the proximal end of the syringe barrel, wherein the control mechanism may rest in contact with the plunger seal. The method may further include, before the step of (ii) mounting a plunger seal through a proximal end of the syringe barrel, the step of: filling the barrel at least partially with a fluid substance. In at least one embodiment, the adapter may be a two component adapter having a proximal adapter portion and a distal adapter portion. The proximal adapter portion may have one or more connection prongs and the distal adapter portion may have corresponding connection ports which, when forced together, connection prongs and corresponding connection ports merge, mate, or otherwise connect to unite the two portions of the adapter. Steps (i) and (ii), and the optional step of filling the barrel at least partially with a fluid substance, may be performed in a sterile environment to maintain the container integrity and sterility of the syringe.

The present invention further provides methods of manufacturing syringes having dose control mechanisms, and methods of operation of such mechanisms and syringes. Such novel devices and methods permit the identification and control of the dosage amount, permit the syringe to be "primed" (i.e., evacuated of air bubbles) prior to drug delivery, and ensure the accurate delivery of microliter volume dosages, all within a device size that is similar to commonly used conventional syringes available in the marketplace.

BRIEF DESCRIPTION OF THE DRAWINGS

The following non-limiting embodiments of the invention are described herein with reference to the following drawings, wherein:

FIG. 5A is a side elevational view of the automatic drug delivery syringe of FIGS. 1-4B illustrating an aspect of the operation of the syringe;

FIG. 5B is an enlarged fragmentary view of the plunger and screw of the automatic drug delivery syringe of FIG. 5A in assembly;

FIG. 5C is an enlarged fragmentary view of engagement of the plunger with the housing of the automatic drug delivery syringe of FIG. 5A;

FIG. 5D is an enlarged fragmentary view of engagement of the screw with the adapter of the automatic drug delivery syringe of FIG. 5A in assembly;

FIG. 5E is an enlarged fragmentary view of assembly of a screw connection aspect with a plunger rod in an embodiment the automatic drug delivery syringe of FIG. 5A;

FIG. 5F is an enlarged fragmentary view of the engagement of the distal end of the locking pin with a locking arm in an embodiment of the automatic drug delivery syringe of FIG. 5A;

FIGS. 5G-5H are a side elevational views of the automatic drug delivery syringe of FIG. 5A including enlarged views of the window and plunger dose markings;

FIG. 6A is an isometric view of an automatic drug delivery syringe according to a second embodiment of the present invention;

FIG. 6B is an enlarged isometric view of the distal portion of the drug delivery syringe shown in FIG. 6A;

DETAILED DESCRIPTION

Figure 1:
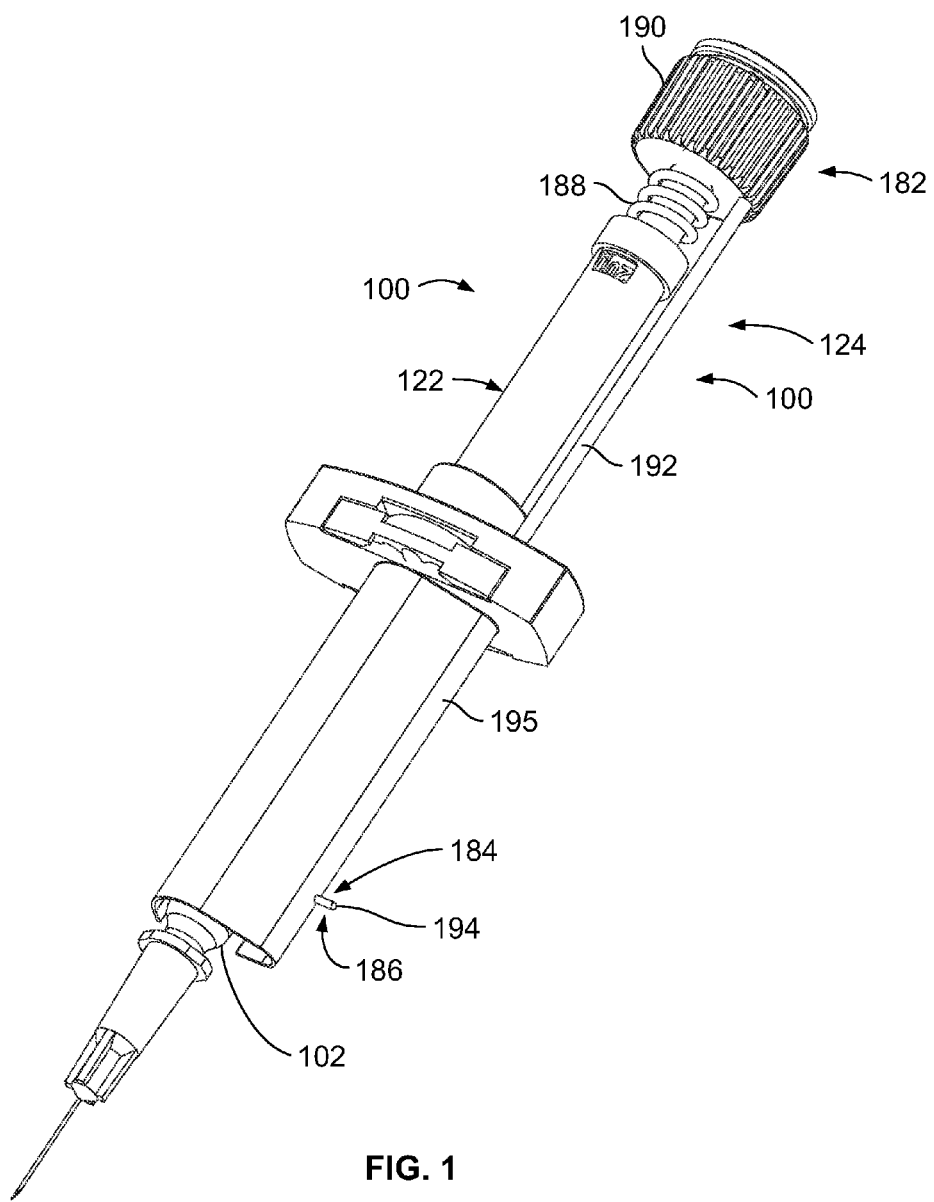
FIG. 1 is an isometric view of an automatic drug delivery syringe, according to at least one embodiment of the present invention.

As used herein to describe the dose control mechanisms, drug delivery syringes, or any of the relative positions of the components of the present invention, the terms "axial" or "axially" refer generally to a longitudinal axis "A" around which the control mechanisms and syringes are preferably positioned, although not necessarily symmetrically therearound. The term "radial" refers generally to a direction normal to axis "A". The terms "proximal," "rear," "rearward," "back," or "backward" refer generally to an axial direction in the direction "P". The terms "distal," "front," "frontward," "depressed," or "forward" refer generally to an axial direction in the direction "D".

As used herein, the term "glass" should be understood to include other similarly non-reactive materials suitable for use in a pharmaceutical grade application that would normally require glass, including but not limited to certain non-reactive polymers such as cyclic olefin copolymers (COC), cyclic olefin polymers (COP), and the like. The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" is not meant to include glass, non-reactive polymers, or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration under ambient temperature and pressure. "Fluid" refers primarily to liquids, but can also include suspensions of solids dispersed in liquids, and gasses dissolved in or otherwise present together within liquids inside the fluid-containing portions of syringes.

According to various aspects and embodiments described herein, reference is made to a "biasing member", such as in the context of one or more biasing members for retraction of a needle or needle assembly. It will be appreciated that the biasing member may be any member that is capable of storing and releasing energy. Non-limiting examples include a spring, such as for example a coiled spring, a compression or extension spring, a torsional spring, and a leaf spring, a resiliently compressible or elastic band, or any other member with similar functions. In at least one embodiment of the present invention, the biasing member is a spring, preferably a compression spring and/or a torsional spring.

Throughout this specification, unless otherwise indicated, "comprise," "comprises," and "comprising," or related terms such as "includes" or "consists of," are used inclusively rather than exclusively, so that a stated integer or group of integers may include one or more other non-stated integers or groups of integers. As will be described further below, the embodiments of the present invention may include one or more additional components which may be considered standard components in the industry of medical devices. The components, and the embodiments containing such components, are within the contemplation of the present invention and are to be understood as falling within the breadth and scope of the present invention.

The novel devices of the present invention automatic self-dispensing accurate dose drug delivery syringes. Such devices may be safe and easy to use, and may be aesthetically and ergonomically appealing for clinical practitioners. The devices described herein incorporate features which may make activation, operation, and lock-out of the device simple for even untrained users. The novel devices of the present invention provide these desirable features while minimizing or eliminating problems associated with known prior art devices. Certain non-limiting embodiments of the novel drug delivery syringes and their respective components are described further herein with reference to the accompanying figures.

Various studies have shown that the accuracy of dose delivery using conventional syringes is affected by a number of factors, including an inability to accurately read and control plunger travel during dosing. The use of conventional drug delivery syringes that have a high dose volume to axial translation ratio (i.e., a significant quantity of drug is dispensed for even incrementally small distances of plunger depression, as may be the case for large diameter syringes) significantly magnifies this inaccuracy. With the growth of high-cost, low-volume drug treatments entering the marketplace, it is increasingly important to accurately dose and deliver such low-volume treatments to the patient. The embodiments of the present invention may overcome the challenges faced with the use of conventional syringes for the dosing and delivery of low-volume treatments by utilizing novel dose control mechanisms. As will be described further herein, the novel dose control mechanisms may permit the user to accurately read and dose the desired volume of drug treatment for delivery to the patient.

FIGS. 1 through 4B show an embodiment of a novel dose control mechanism 100 for a syringe 102, according to at least one embodiment of the present invention. The syringe 102 may be of any appropriate design and may include, for example, an elongated hollow barrel 104 having a distal end 106 and a proximal end 108. A barrel adapter assembly 110 disposed at the distal end 106 of the barrel 104 couples a needle assembly 112 to the barrel 104, and a plunger seal 114 is disposed within the hollow interior of the barrel 104.

Figure 7A:
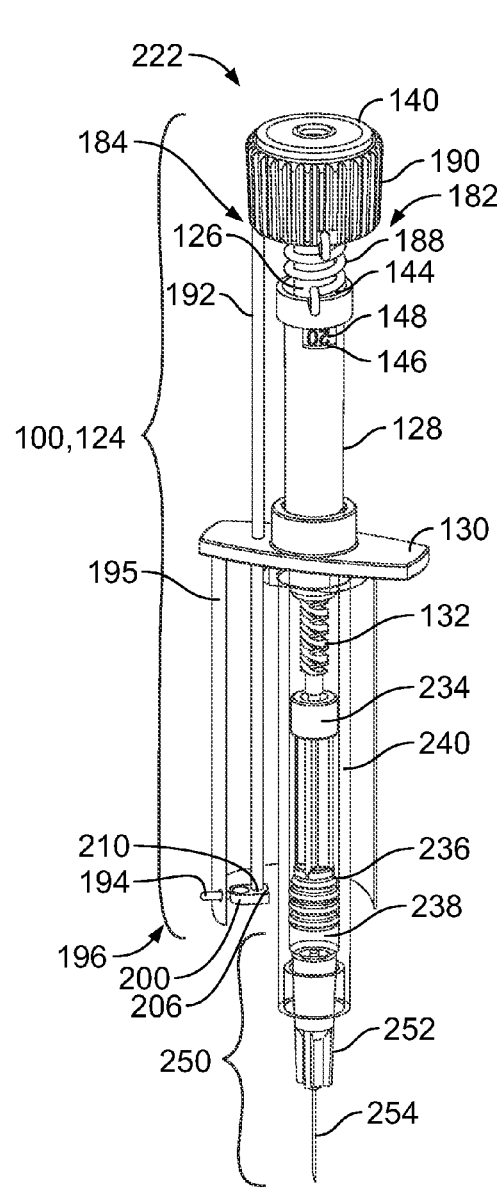
FIG. 7A is an isometric view of an automatic drug delivery syringe according to a third embodiment of the present invention.
Figure 7B:
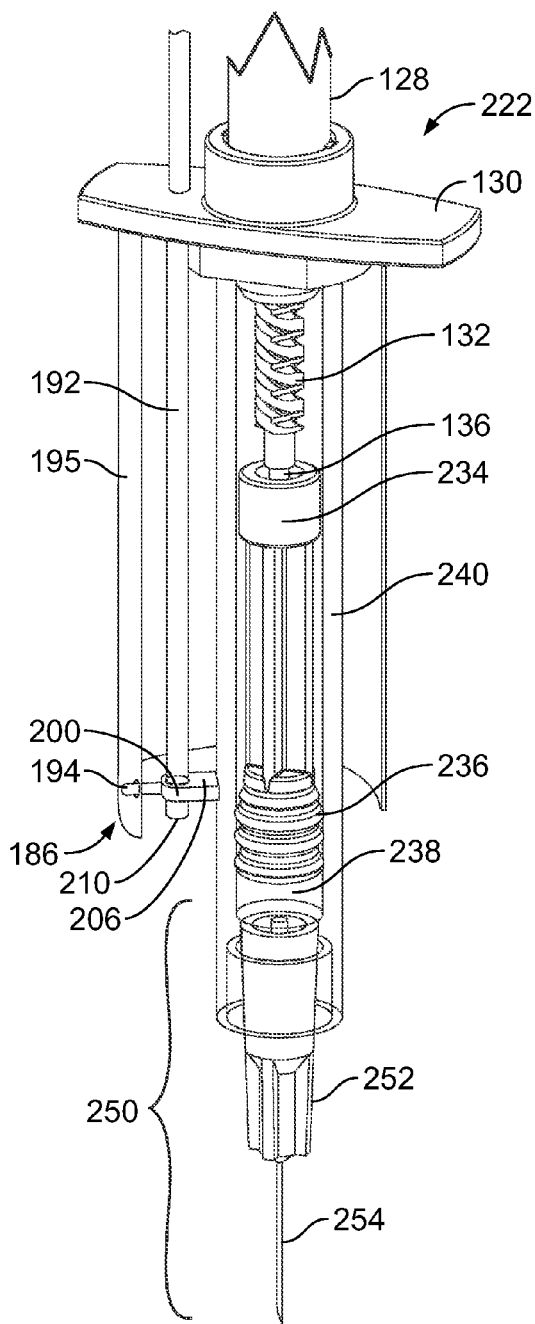
FIG. 7B is an enlarged isometric view of the distal portion of the drug delivery syringe shown in FIG. 7A.

The barrel adapter assembly 110 may be attached, mounted, affixed, or otherwise connected to the distal end 106 of the barrel 104 by a number of known methods, such as Luer connections, interference fit connections, barrel adapter connections, or any number of other known connections. For example, a luer connection may be utilized to connect the barrel adapter assembly 110 to the syringe barrel 104. Luer connection systems are a standard way of attaching syringes, catheters, hubbed needles, IV tubes, and the like to each other. Luer connections consist of conical/tubular male and female interlocking components slightly tapered to hold together better. Luer connections can either be a "luer slip", as shown in FIGS. 6A and 6B, which are luer connections with a simple pressure or twist fit; luer connections be a "luer lock", as shown in FIGS. 7A and 7B, which can have an additional outer rim of threading allowing them to be more secure. The type of connections described herein can be utilized regardless of the type of syringe with which they are shown. For clarity, the luer slip connection shown with the fill-at-time-of-use syringe in FIGS. 6A and 6B may be utilized with the pre-filled syringe in FIGS. 7A and 7B, or any other type of connection may be used with any other type of syringe described herein. Alternatively, the connection may be facilitated by a barrel adapter connection. By way of example, the barrel adapter connection may be as described in International Publication WO2011/137488 and/or U.S. patent application Ser. No. 13/693,915, although without limitation thereto.

Returning to FIG. 2A, regardless of the type of barrel adapter assembly 110 utilized, the barrel adapter assembly 110 generally comprises of a barrel tip 116 and the needle assembly 112, which includes a needle 118. In some configurations, the barrel tip 116 may be a pre-formed aspect at the distal end of the barrel 104. Alternatively, the barrel tip 116 may be a separate component that is attached at the distal end of the barrel 104, as described, for example, above. The needle 118 may be any type of fluid conduit including, for example, a flexible cannula or a rigid needle, and may be made of any number of materials, including stainless steel.

Similarly, the plunger seal 114 may be of any appropriate material or design. The hollow interior of the barrel 104, along with the plunger seal 114 and the barrel adapter assembly 110 form a drug chamber 120 within the syringe 102. Axial translation of the plunger seal 114 in the distal direction within the hollow interior of the barrel 104 forces drug fluid out of drug chamber 120, through the needle 118 of the barrel adapter assembly 110, for injection and delivery to the patient.

While the syringes of the various embodiments herein will not be described in greater detail in each of the descriptions of the embodiments below, those of skill in the art will appreciate that the syringe design utilized may be of any suitable design.

The dose control mechanism 100 includes a plunger assembly 122 and an automatic administration assembly 124. While the plunger assembly 122 may include an interface for manual drug administration, the automatic administration assembly 124 may be utilized in conjunction with the plunger assembly 122 to provide an automatic, controlled administration of a drug from the drug chamber 120 when actuated.

In order to provide enhanced control of the volume of drug administered, the plunger assembly 122 may include structure that limits the relative speed with which a volume of drug administered as a result of travel of the plunger assembly 122. This structure, in conjunction with the automatic administration assembly 124 provides a very controlled administration of drug from the drug chamber 120. While the exemplary plunger assembly illustrated includes speed/volume control structure with the automatic administration assembly, it will be appreciated that alternate plunger assemblies may be utilized in conjunction with the automatic administration assembly, either with or without such speed/volume control.

The plunger assembly 122 of FIGS. 2A through 4B includes a plunger 126, a housing 128, an adapter 130, and a screw 132. The housing 128 has a substantially cylindrical axial pass-through within which the substantially cylindrical plunger 126 may at least partially reside. Housing 128 may optionally include housing cover 144 at its proximal end, for example, to close the interior of the housing 128 off from the environment and/or to axially align plunger 126 within housing 128, and to prevent removal of the plunger rod by functioning as a mechanical stop. The housing cover 144 may be a pre-formed aspect of the housing 128 or may be a separate component from the housing 128.

The distal end of the housing 128 is connected to, and/or resides partially within, a proximal portion of adapter 130. The housing 128 may be coupled to the adapter 130 by any appropriate arrangement, such as, for example, screw threads, as illustrated in this embodiment. The proximal and distal portions of adapter 130 may be separated by an adapter flange 134 which may additionally serve as a finger flange for use by the user. Screw 132 may reside at least partially within housing 128 and plunger 126, and extend distally beyond flange 134. Screw 132 may have a screw connection aspect 136 to facilitate integration of the control mechanism with a drug delivery syringe 102 and to center the plunger 126. The internal aspects of these components will be described in further detail herein below.

The plunger 126 is an elongated substantially cylindrical structure, and may include a button 140 for engagement by a user. The button 140 may be a pre-formed aspect of the plunger 126 or may be a separate component from the plunger 126. For example, button 140 may be a preformed aspect at the proximal end of the plunger 126. Alternatively, button 140 may be a separate component attached to the proximal end of plunger 126 by a snap-fit, such as in the embodiment illustrated in FIGS. 3A-4B. In a preferred embodiment, the button 140 may be attached to plunger 126, but allowed to axially rotate freely from plunger 126. In this way, the button 140 may be rotationally fixed relative to the user's/clinician's finger during depression of the plunger 126 when such plunger is utilized in a manual form of operation. Regardless of the specific configuration and relationship of button 140 and plunger 126, button 140 is intended to have a user interface surface 142 for contact and control by a user (e.g., such as with the thumb or finger tip of the user) during manual administration of a drug, as opposed to automated delivery.

Housing 128 may further include a window 146, which may be an opening (e.g., an aperture) in the housing or a transmissive or translucent component. Regardless of the particular configuration of window 146, its primary purpose is to permit the user to view the location of the plunger 126 within housing 128. Plunger 126 may include one or more dose markings 148 on the external surface of the plunger 126. Housing 128 may have one or more reference or guide markings 150, such as at the window 146, with which to align plunger dose markings 148. The plunger dose markings 148 may correspond to the relevant dose amounts desired by the user. By employing the respective plunger and housing markings, the user can identify volumetric dose quantities desired for controlled delivery to the patient, as will be explained further herein. In another embodiment, the window 146 may be covered by a lens, such as a clear lens, that provides visual magnification.

Figures 3A, 3B:
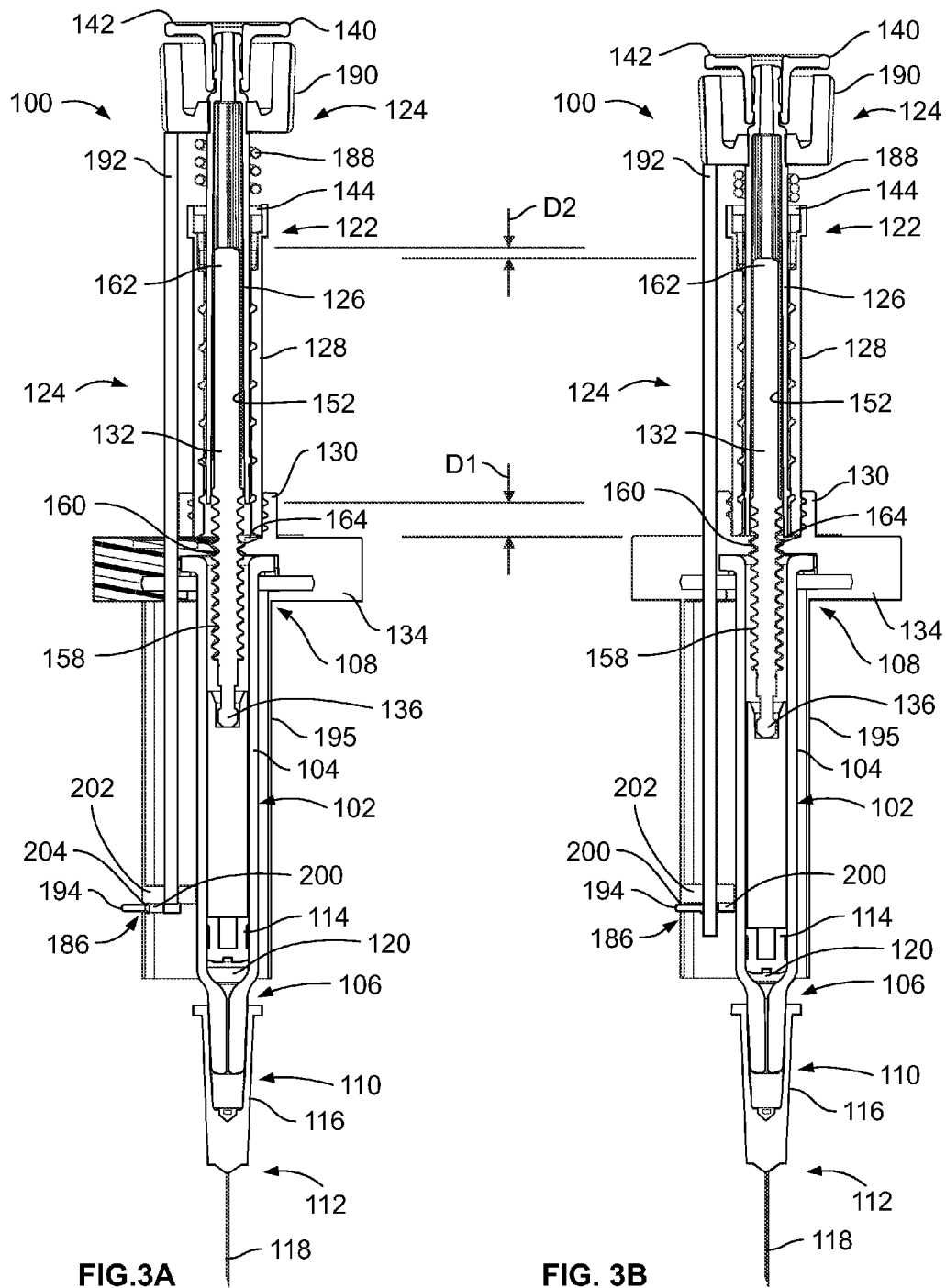
FIG. 3A is a cross-sectional view of the automatic drug delivery syringe of FIGS. 1-2B as the components may appear in a ready-to-inject stage of operation.
FIG. 3B is a cross-sectional view of the automatic drug delivery syringe of FIGS. 1-3A as the components may appear in an end-of-dose stage of operation.
Figure 4A:
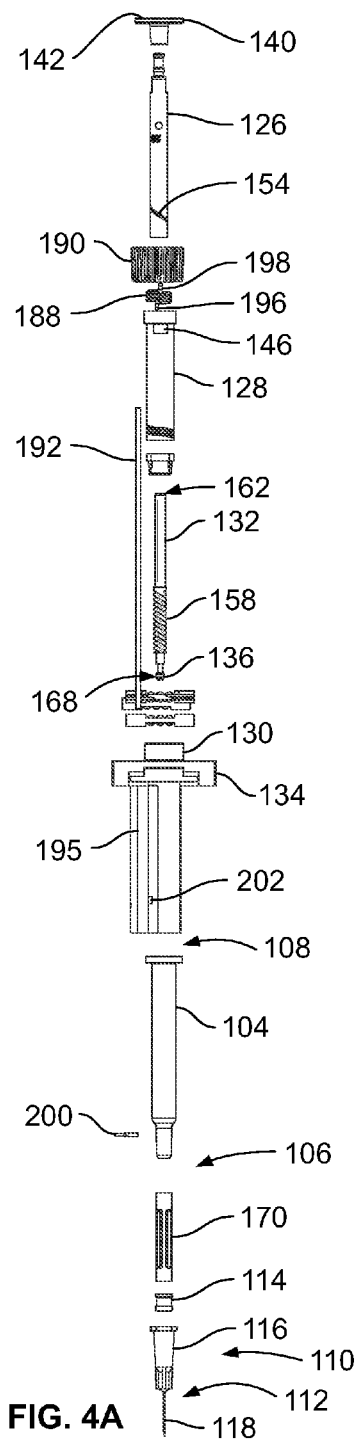
FIG. 4A is an exploded view of the automatic drug delivery syringe of FIGS. 1-3B.
Figure 4B:
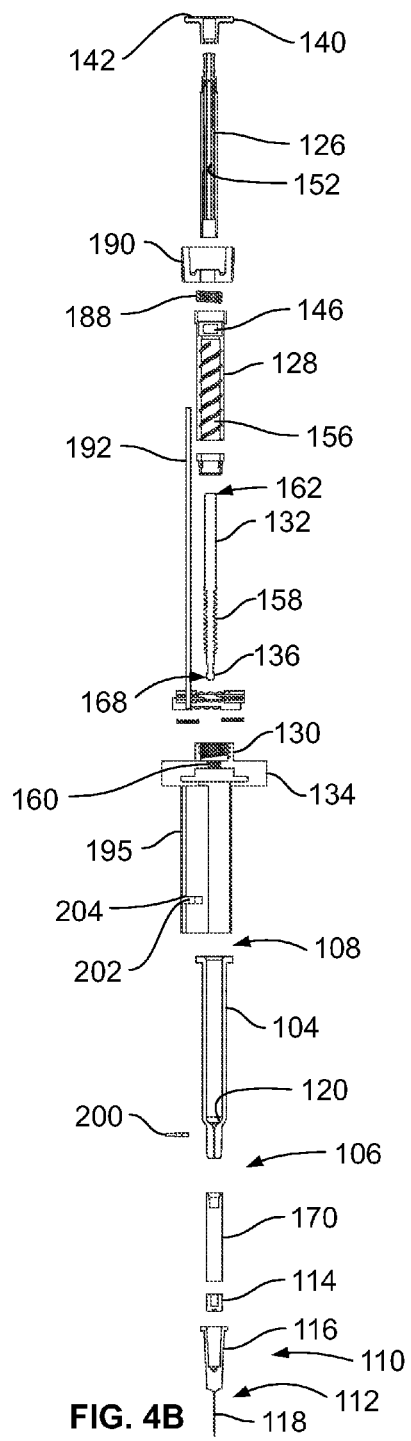
FIG. 4B is the exploded view of FIG. 4A in cross-section.

FIGS. 3A and 3B show cross-sectional views of the dose control mechanism, according to at least one embodiment of the present invention, in a ready-to-inject stage and in an end-of-dose stage, respectively. The cross-sectional views show certain other aspects of the components which are internal to the mechanism. The plunger 126 has a coarse pitch male thread 154 (visible in FIG. 4A) on its exterior surface which interfaces with the coarse pitch guide 156 along the interior surface of the housing 128 such that, in at least one embodiment, the pitch on guide 156 is the same as pitch on plunger thread 154 (see also FIG. 5C). The terms "male" and "female" are intended to describe corresponding and interfacing threads or surfaces, and can be used interchangeably to describe corresponding aspects as would be readily appreciated in the art.

Figures 2A, 2B:
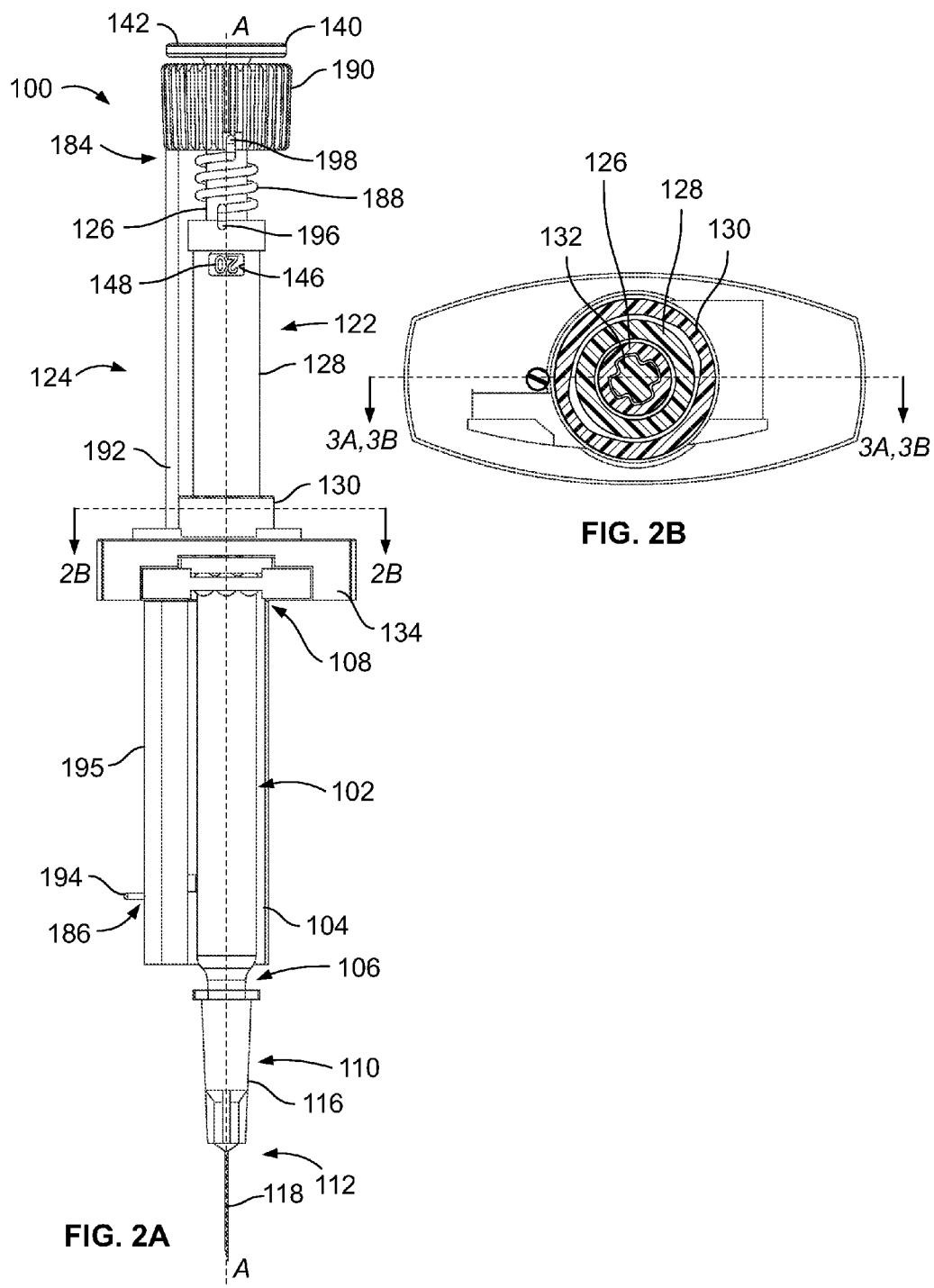
FIG. 2A is a side elevational view of the automatic drug delivery syringe of FIG. 1.
FIG. 2B is a cross-sectional view of the automatic drug delivery syringe taken along line 2B-2B in FIG. 2A.

The plunger 126 has an internal annular space 152 within which screw 132 at 10 least partially resides. Both screw 132 and plunger 126 reside, at least partially and/or at some point of operation, within housing 128. In order impart rotational movement of the plunger 126 to the screw 132, the plunger 126 and a proximal portion of the screw 132 are rotationally keyed to one another. The term "keyed" is used herein to mean any number of internal aspects which removably or slidably (in the axial sense) connect two or more components. For example, the plunger 126 may be a hollow cylinder having a coarse pitch screw on at least some portion of the outer surface and a spline design along at least a portion of the inner surface. The spline design is configured to mate with, and transform or relay rotation to, a complimentary spline contained at a proximal end of the screw 132. This spline design element ensures that the plunger 126 and screw 132 are rotationally keyed. The spline or rotationally keyed aspect is visible at the proximal end 162 of screw 132, and with its corresponding spline or rotationally keyed aspect in the annular space 152 of plunger 126 in FIG. 2B. As shown in FIGS. 2B and 5B, in at least one embodiment, screw 132 has a cross or plus shape in its perpendicular cross-section which is keyed to plunger 126. This arrangement or configuration allows the two components to be rotationally keyed while allowing them to axially slip past each other. While the illustrated embodiment includes a cross or plus shape, any number of corresponding shapes may be utilized to impart a rotationally "keyed" relationship between these components such that the first component may removably or slidably engage the second component in a manner which enables the rotational keyed relationship and permits axial slip. Such components may alternatively be keyed to have the shape of, for example, a horizontal line or minus, a star, or a semi-circle shape, with the corresponding component having the inverse of the shape on an interior annular space.

In a manner similar to the plunger 126, a distal portion 168 of the screw 132 includes a fine pitch thread 158 which interfaces with a fine pitch nut 160 of adapter 130 such that, in at least one embodiment, the pitch on screw thread 158 is the same as pitch on nut 160 (see also FIG. 5D). Also visible in FIGS. 3A and 3B are the proximal end 162 of screw 132 and abutment surface 164 of adapter 130. The plunger 126 having the coarse pitch male thread 154 is rotatable upon the corresponding (e.g., "female") coarse pitch guide 156, which is rotationally keyed to the screw 132 having the fine pitch thread 158. Because the plunger 126 and screw 132 are rotationally keyed, each having a respective screw pitch, rotational translation of the plunger 126 rotates and axially translates the screw 132. The screw 132, having the fine pitch screw thread 166, engages the female fine pitch nut 160 of the adapter 130. Hence, rotation of plunger 126 results in axial translation of screw 132 and the resolution of axial travel is dictated by fine pitch thread 158 of the screw 132.

Fine pitch nut 160 (or simply "nut"), having the same fine pitch of the screw 132, may be used to brace the screw 132 and facilitate the transfer of the rotational movement of the plunger 126 into axial translation of the screw 132. The pitch ratio of the coarse pitch to the fine pitch dictates the degree or resolution of axial travel of the screw 132, i.e., the distance that the screw 132 axially translates for each rotation of the plunger 126. As a result, the medical practitioner is provided with an ease of operation that enables them to accurately read and set the dosage amount. The pitch ratio can be set to enable "fine tuning" of the dosage amount, which is of particular importance for low-volume dosage quantities where variance may be significantly affected by plunger travel.

During operation of the dose control mechanism, the user may axially rotate plunger 126 to control the desired dosage volume for injection into the patient. Axial rotation of the plunger 126 causes coarse pitch male thread 154 (visible in FIG. 3B) to travel within the corresponding coarse pitch guide 156 of housing 128, as shown in FIGS. 3A and 3B. This action causes the plunger 126 to axially translate in the distal direction thereby reducing the dosage volume within the drug chamber, as is explained in more detail herein. Because of the rotationally keyed interaction between plunger 126 and screw 132 within the annular space 152, rotation of the plunger 126 causes screw 132 to axially rotate and translate. However, because of the pitch ratio between the plunger 126 and screw 132, each unit measure of translation in the distal direction of the plunger 126 results in fractional (e.g., smaller, more resolved) translation of the screw 132 in the distal direction. Because of the pitch ratio between the plunger 126 and the screw 132, as plunger 126 is depressed or axially translated in the distal direction (i.e., in the direction of solid arrow in FIGS. 3A and 3B), screw 132 is caused to axially translate in the distal direction only a fraction of the distance translated by the plunger 126. This difference in axial translation distance between plunger 126 and screw 132 is visible by comparing distances D1 and D2 in FIGS. 3A and 3B. D1 is the distance that plunger 126 axially translates while D2 is the incremental distance that screw 132 axially translates. The difference in dimensions D1 and D2 is also clear by the reduction in the annular space 152 within the plunger 126 above the proximal end 162 of the screw 132. It is noted that the variable annular space 152 within the plunger 126 is related to the mechanical set-point desired by the practitioner and provides space for translation of the screw 132 during the dosage stroke. This has a number of benefits for accurate control during delivery of low-volume doses. Primarily, the pitch ratio relationship permits the user to accurately control the desired dose and delivery of a drug treatment.

In order to provide axial, translational movement of the screw 132 to the plunger seal 114 without the rotational movement of the screw 132, the screw 132 may be coupled to the plunger seal 114 by any appropriate coupling structure to either directly or indirectly drive the axial translation of the plunger seal 114. In the embodiment of FIGS. 3A-4B, a plunger rod 170 is coupled to both the screw 132 and the plunger seal 114. The plunger rod 170 may be connected to the screw 132 at, for example, at a screw connection aspect 136. In this embodiment, the screw connection aspect 136 is a ball-like structure that is received within a socket 174 of the plunger rod 170 to provide a ball-and-socket joint. Optionally, a ring 138 may be provided near the distal end of the screw 132, which may be utilized to facilitate the connection of the screw 132, the plunger rod 170 and the plunger seal 114. Referring the enlarged view of FIG. 5E, in at least one embodiment, the screw connection 172 aspect is connected to the plunger rod 170 through a radial opening 176 in the plunger rod 170. Additionally or alternatively, this connection may be a snap-fit connection, as illustrated in FIGS. 3A-3B, an interference-fit connection, or a number of other connection methods known in the industry. In at least one other embodiment, the screw connection aspect is connected to the plunger rod through a proximal opening in the plunger rod such that the screw connection aspect sits within a proximal pocket in the plunger rod.

Preferably, the connection between the screw 132 and the plunger seal 114, or screw 132 and plunger rod 170 when a plunger rod is employed, is such that the screw is permitted to axially rotate while the plunger rod 170 and/or the plunger seal 114 remain rotationally fixed. Accordingly, as the plunger 126 and screw 132 of the control mechanism 100 are axially rotated and translated, the motion is relayed to the plunger seal 114 which is also axially translated.

In accordance with the invention, the dose control mechanism 100 further includes automatic administration assembly 124. By way of the automatic administration assembly 124, the user may preselect the volume of drug to administer, then actuate the dose control mechanism 100 to deliver the drug without the user physically depressing the plunger 126. The automatic administration assembly 124 includes an administration mechanism 182, a locking mechanism 184, and an actuator 186.

In the embodiment illustrated in FIGS. 1-5A, the automatic administration assembly 124 includes a biasing member 188, a selection dial 190, a locking pin 192, and a dispense button 194. In order to support the dispense button 194 and the locking pin 192, the automatic administration assembly 124 may further include an automation housing 195. The automation housing 195 may be formed as a separate component, or may be unitarily formed with or secured to the adapter 130.

In this embodiment, the administration mechanism 182 includes the selection dial 190 and the biasing member 188. As may best be seen in FIGS. 1, 2A, 3A and 3B the selection dial 190 is disposed subjacent the button 140 and is secured to the plunger 126. Accordingly, rotation of the selection dial 190 causes a corresponding rotation of the plunger 126. Thus, by rotating the selection dial 190, the user may adjust the dose to be administered, viewing the selected dose by way of the plunger dose markings 148 visible in the window 146. As shown in FIG. 5G, for example, the plunger dose markings 148 may include a numerical value corresponding to the volume of drug to be administered.

The illustrated biasing member 188 of this embodiment is a torsion spring. It will be appreciated, however that the biasing member may be of an alternate design, such as a compression spring. The biasing member 188 is disposed about the plunger 126, and includes an anchor end 196 and a rotatably mounted end 198. As illustrated in FIG. 2A, the anchor end 196 is coupled to the housing 128, while the rotatably mounted end 198 is coupled to the selection dial 190. As a result, as the selection dial 190 is rotated to provide the desired dose (as shown by the arrow in FIG. 5A), the rotatably mounted end 198 of the biasing member 188 rotates with the selection dial 190, biasing the selection dial 190 to dispense the drug from the syringe 102.

In order to maintain the selection dial 190 in the pre-dispensing position, the locking pin 192 is disposed against the selection dial 190. The locking pin 192 is maintained in position against the selection dial 190 by a slidably mounted locking arm 200. As may best be seen in FIG. 5F, the locking arm 200 may be supported by the automation housing 195, which may include one or more support flanges 202. While in this embodiment the locking arm 200 extends through an aperture 204 in a wall of the automation housing 195 with a single support flange 202 above the locking arm 200, it will be appreciated that a second support flange may be provided, for example, subjacent the locking arm 200. It will be appreciated that the illustrated support flange 202 disposed above the locking arm 200 includes an aperture through which the locking pin 192 may extend. Referring again to FIG. 5F, the locking arm 200 may include an abutment surface 206, and an actuation opening 208. In this way, when the abutment surface 206 is disposed subjacent a distal end 210 of the locking pin 192, the locking pin 192 is held in position against the selection dial 190. Conversely, when the actuation opening 208 is moved to a position subjacent the distal end 210 of the locking pin 192, the locking pin 192 is permitted to move through the actuation opening 208 under the biasing force of the biasing member 188. While the actuation opening 208 may fully correspond to the outer surface of the locking pin 192, it will be appreciated that the actuation opening 208 may alternately be an arcuate opening, for example, in a side surface of the locking arm 200, so long as that actuation opening 208 is of a shape and size that allows the free passage of the locking pin 192.

The locking arm 200 further includes the dispense button 194 that extends from the outer surface of the automation housing 195. Thus, by depressing the dispense button 194, the user may move the actuation opening 208 to the position subjacent the distal end 210 of the locking pin 192, allowing the movement of the locking pin 192 out of engagement with the selection dial 190. In this embodiment, the dispense button 194 30 is disposed substantially adjacent the distal end of the syringe 102, with the locking pin 192 extending substantially parallel to the syringe 102. In order to support the locking pin 192, an aperture may be provided through the adapter flange 134. One or more additional support flanges 202 may be provided within the automation housing 195. It will be appreciated that the positioning of the dispense button 194 toward the end of the syringe 102 allows a user to hold the syringe 102 much like a pen, actuating the actuator 186 only when the needle 118 is disposed in a desired position. Those of skill will further appreciate, however, that the actuator 186, here, dispense button 194 may be alternately positioned.

In use, the user first selects the desired volume of drug to be delivered using the selection dial 190 (see FIGS. 5A and 5G). The rotation of the selection dial 190 energizes the biasing member 188, while the locking pin 192 held between the selection dial 190 and the abutment surface 206 of the locking arm 200, that is, the locking mechanism 184, locks the selection dial 190 with the biasing member 188 in the energized position. Upon a desired placement of the needle 118, the dispense button 194 (see FIG. 5F) is depressed to actuate dispensing of the drug. With the selection dial 190 no longer held in position, the biasing member 188 deenergizes, imparting rotation to the plunger 126. As explained in detail above, as the plunger 126 rotates by way of its course pitch thread 154 along the course pitch guide 156 of the housing 128 (see FIG. 5C), the rotationally keyed screw 132 (see FIG. 5B) rotates along its fine pitch thread 158 engaged with the fine pitch nut 160 of the adapter 130 (see FIG. 5D). The translational, axial movement of the screw 132 is transmitted to the plunger seal 114, here, by way of plunger rod 170 (see FIG. 5E) to dispense the drug.

The novel syringes of the present invention may also utilize features which provide integrated and adjustable range-of-travel limits to ensure accurate delivery of low-volume drug treatments. This may be enabled, for example, by incorporating features that prevent variable depression of the plunger seal (or stopper) (e.g., preventing the plunger from "bottoming out" during drug delivery) within a syringe. Specifically, the dose control mechanisms of the present invention utilize adjustable set mechanical end-points for the range of plunger axial travel during drug delivery. Such limits may be predefined, i.e., integrated and fixed into the syringe configuration in advance of use by the medical practitioner, or adjustable, i.e., variably controlled by a compounding pharmacist, a medical practitioner, or by a self-administering patient using an integrated dosage setting mechanism. Such mechanical set-points permit a range of axial plunger travel that are, for example, related to the priming and dosing quantities, but also prevent the user from variably depressing the plunger and plunger seal as part of the dosing stroke or from bottoming out these components within the dosing chamber of a syringe. This novel control mechanism greatly increases the accuracy of the dose delivered to the patient. Additionally, embodiments of the present invention allow the user to prime the syringe to evacuate the dosing chamber of any residual air prior to delivering the dose to the patient. The prime step may be a fixed amount or a variable amount, depending on the configuration of the low dose syringe and variation in amount of drug or liquid contained/filled in the dosing chamber. The configuration of the novel syringe allows the user to complete the prime step while maintaining, or enabling, the ability of the syringe to deliver an accurate and precise dose to the patient.

As stated above, the mechanical set-point limits effectively function to prevent the user from variably depressing the plunger and plunger seal or from bottoming out 10 these components within the dosing chamber of a syringe. This functionality increases the accuracy of the dose delivered to the patient because it reduces the variability of the delivered dose from the amount prescribed and intended to be delivered to the patient. The mechanical end-points may be readily identified and easily set by employing the pitch ratio between the plunger 126 having a coarse pitch thread 154 and the screw 132 having a fine pitch thread 158. For example, in one such embodiment a pitch ratio between the coarse pitch and a fine pitch may be 4:1, such that rotationally "screwing" or turning the selection dial 190 and associated plunger 126 axially translates the plunger component four times as far as the axial translation of the screw component. Accordingly, the practitioner is provided with a significant ease of operation since they may more accurately set the required dosage amount. Such a pitch ratio may be, for example, anywhere from the range of 1:1 to 20:1, as may be necessary to obtain the required accuracy of the low-volume dosage amount. The "dialing-in" or "setting" may be facilitated by the dose markings on the plunger and guide markings on the housing described above.

As the biasing member 188 deenergizes, causing the rotation of the plunger 126 set the desired low-volume dosage for injection, the user can perform what is known in the art as a "priming step." This priming step evacuates the dosing chamber of any residual air bubble captured in the dosing chamber during pre-filling, if any, and primes the attached needle (or catheter or an extension set) before delivery. After priming and setting of the dose has been completed, the dispense button 194 may be depressed allowing delivery of the drug, the plunger seal 114 advancing inject the desired dose amount to the patient. Upon drug dose delivery, the plunger 126 is caused to "bottom out" on the abutment surface 164 of the adapter 130 (as shown in FIG. 3B). Upon completion of the delivery, the plunger dose marking 148 appearing in the window 146 may include a representation that that delivery is complete, as, for example, the dot illustrated in FIG. 5H.

Notably, the novel embodiments contemplated by the present invention effectively prevent the plunger seal from "bottoming-out" within the dosing chamber. This feature along with the automatic administration assembly 124 may pre-empt one aspect of user variability in either excess dosing by over-depression of the plunger or under dosing by under-depression of the plunger, ensuring that the quantity dosed to the patient is accurate and minimizes user error. This is of particular importance in low dosage treatments, where user-related errors can cause significant and undesirable variation and inaccuracy in the delivery of medication to the patient. The embodiments according to the present invention may prevent such occurrences and work to effectively eliminate the dosing errors associated with prior syringe configurations and delivery methodologies. Furthermore, depression of the plunger in this embodiment does not back-drive the screw.

It will be appreciated that the various components of the automatic administration assembly 124 may vary. For example, the administration mechanism 182, the locking mechanism 184, and the actuator 186 may be of alternate designs.

The novel dose control mechanisms 100, and automation assemblies 124 of the present invention can be integrated into a number of drug delivery syringe configurations to provide accurate dose delivery capability to the user. They may additionally be incorporated into existing syringes, either as integral or supplemental features. For example, these components may be configured to operate with the dose control mechanisms as described in International Publication WO2013/086167, although without limitation thereto. For example, the control mechanisms may be utilized with fill-at-time-of-use syringes, pre-filled syringes, or safety syringes having integrated needle retraction or needle sheathing safety features, or a combination thereof.

Figure 8A:
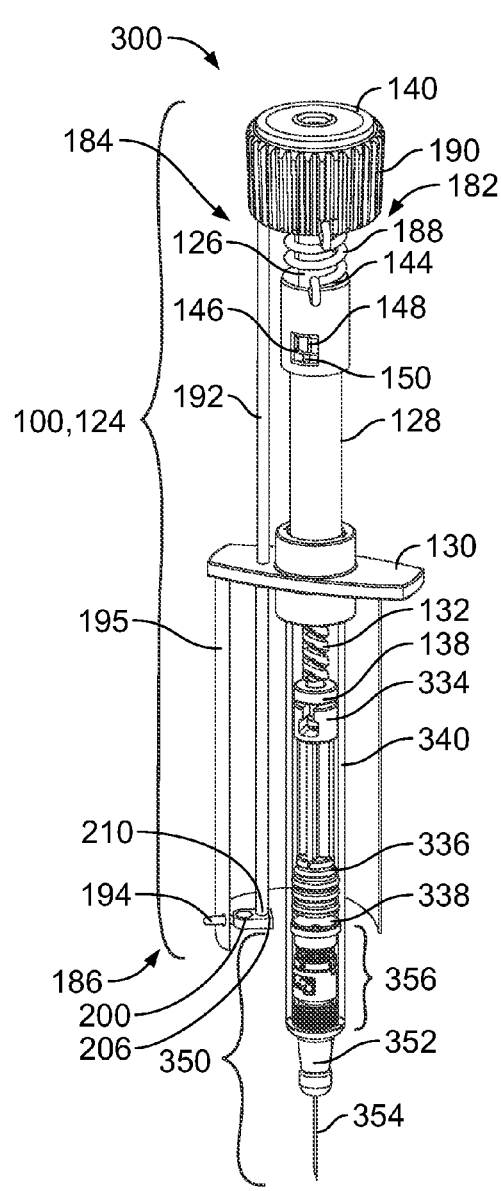
FIG. 8A is an isometric view of an automatic drug delivery syringe according to a fourth embodiment of the present invention.

The components utilized and shown with reference to the syringe of FIG. 1 may similarly be utilized with the syringes of FIGS. 6A, 7A, 8A, and/or 9A, as would readily be appreciated by an ordinarily skilled artisan. Examples of such syringes which incorporate the novel dose control mechanisms are provided below. For ease of understanding, like components in the embodiments of FIGS. 6A, 7A, 8A and 9A utilize like numbers to those component within the earlier embodiment. Thus, by employing the automatic administration assembly 124 with the respective plunger 126 and, optionally, the dose markings 148 and guide markings 150, the user can control the volumetric dose quantities within the syringe that is desired and provide automatic delivery to the patient. The plunger dose markings 148 may correspond to the relevant dose amounts desired by the user. The user may initially utilize the plunger 126, such as by rotating the plunger 126, to identify and select the desired dose amount by aligning the desired dose marking 148 with the guide marking 150. Axial rotation of the plunger 126 causes the plunger 126 to axially translate, which motion is transferred by the above described mechanism to the screw 132. Axial translation of the screw 132 in the distal direction causes drug fluid contained within the drug chamber of the syringe to be dispensed through the needle 118 of the barrel adapter assembly 110.

Typically, once the desired dose has been identified and selected by the user, the remaining amount of drug fluid within the drug chamber 120 is substantially the exact amount desired to be injected. The needle 118 may then be disposed in the target tissue and by the administration mechanism 182 initiated by actuating the actuator 186 to unlock the locking mechanism 184 to deliver the drug to the target tissue. In the embodiments of the present invention intended for fill-at-time-of-use syringes, the plunger 126 and screw 132 may initially function in reverse (e.g., axially translate in the proximal direction) to draw-in drug fluid from a vial or container to fill the drug chamber of the syringe. In the embodiments of the present invention intended for retractable or safety syringes, the plunger 126 and screw 132 may function, substantially after the drug dose has been delivered, to initiate or engage a needle retraction or safety mechanism. These embodiments of the present invention are discussed in further detail below with reference to the accompanying figures.

Turning now to FIG. 6A, there is illustrated an exemplary fill-at-time-of-use syringe 220 incorporating an embodiment of the dose control mechanism 100 and automatic administration assembly 124, i.e., syringes which can be drawn back and filled with a drug treatment by the user. As with the embodiment of FIGS. 2A-4B, the control mechanism 100 includes a plunger 126, a housing 128, an adapter 130, and a screw 132 essentially as described above, including all possible modifications. The plunger 126 may include a button 140 as a unified or separate component. The housing 128 may optionally include housing cover 144 at its proximal end, for example, to close the interior of the housing 128 off from the environment and/or to axially align plunger 126 within housing 128. The housing 128 may further include a window 146, which may be an opening (e.g., an aperture) in the housing or a transmissive, translucent, and/or optically magnifying component. The plunger 126 may include one or more dose markings 148 on the external surface of the plunger 126. The housing 128 may have one or more reference or guide markings, such as at the window 146, with which to align plunger dose markings 148. The control mechanism 100 may be attached, mounted, affixed, or otherwise connected at the proximal end of barrel 104 such that at least a portion of the screw 132 resides inside barrel 104.

FIG. 6B shows an enlarged isometric view of the distal portion of the drug delivery syringe 220 shown in FIG. 6A. The screw 132 may be connected to plunger seal 114 either directly or indirectly to drive the axial translation of the plunger seal 114. In the latter configuration, a plunger rod 170 may be utilized between screw 132 and plunger seal 114 to connect those components. The plunger rod 170 may be connected to the screw 132 at, for example, the screw connection aspect 136. Optionally, a ring 138 near the distal end of the screw 132 may be utilized to facilitate the connection of the screw 132, the plunger rod 170 and the plunger seal 114. In this embodiment, a ring 138 is provided to facilitate integration of the control mechanism 100 with the syringe 220, and center the distal portion 168 of the screw 132 within the barrel 104. In at least one embodiment, the screw connection aspect 136 is coupled to the plunger rod 170 through a radial opening in the plunger rod, as illustrated in FIGS. 6A-6B. Additionally or alternatively, this connection may be a snap-fit connection, an interference-fit connection, or a number of other connection methods known in the industry. In at least one other embodiment, the screw connection aspect is connected to the plunger rod through a proximal opening in the plunger rod such that the screw connection aspect sits within a proximal pocket in the plunger rod. Preferably, the connection between the screw 132 and the plunger seal 114, or screw 132 and plunger rod 170 when a plunger rod is employed, is such that the screw is permitted to axially rotate while the plunger rod and/or the plunger seal remain rotationally fixed. Accordingly, as the plunger 126 and screw 132 of the control mechanism 100 are axially rotated and translated, the motion is relayed to the plunger seal 114 which is also axially translated.

In accordance with the invention, the dose control mechanism 100 further includes automatic administration assembly 124 substantially as described with regard to FIGS. 2A-4B. By way of the automatic administration assembly 124, the user may preselect the volume of drug to administer, then actuate the dose control mechanism 100 to deliver the drug without the user physically depressing the plunger 126. The automatic administration assembly 124 includes an administration mechanism 182, a locking mechanism 184, and an actuator 186.

In this embodiment, the automatic administration assembly 124 includes a biasing member 188, a selection dial 190, a locking pin 192, and a dispense button 194, here, further supported by an automation housing 195, which may be formed as a separate component, or may be unitarily formed with or secured to the adapter 130.

In this embodiment, the administration mechanism 182 includes the selection dial 190 and the biasing member 188, substantially as described above. Accordingly, rotation of the selection dial 190 causes a corresponding rotation of the plunger 126. Thus, by rotating the selection dial 190, the user may adjust the dose to be administered, viewing the selected dose by way of the plunger dose markings 148 visible in the window 146.

In order to maintain the selection dial 190 in the pre-dispensing position, the locking mechanism 184 includes the locking pin 192 is disposed against the selection dial 190 and maintained in position against the selection dial 190 by a slidably mounted locking arm 200. Depression of the actuator 186, that is, the dispense button 194, moves the abutment surface 206 out of engagement with the distal end 210 of the locking pin 192, allowing the locking pin 192 to move out of engagement with the selection dial 190.

Similarly, the novel control mechanisms of the present invention may be utilized with pre-filled syringes, i.e., syringes which are filled with a drug treatment by the manufacturer and ready for injection by the user. FIG. 7A shows an embodiment of the dose control mechanism 100 as a component of an exemplary pre-filled drug delivery syringe 222. As shown, the control mechanism 100 includes a plunger 126, a housing 128, an adapter 130, and a screw 132. Housing 128 may optionally include housing cover 144 at its proximal end, for example, to close the interior of the housing 128 off from the environment, to axially align plunger 126 within housing 128, and/or to prevent the plunger 126 being accidently removed by the user/clinician. Housing 128 may further include a window 146, which may be an opening (e.g., an aperture) in the housing or a transmissive or translucent component. Plunger 126 may include one or more dose markings 148 on the external surface of the plunger 126. Housing 128 may have one or more reference or guide markings, such as at the window 146, with which to align or view plunger dose markings 148. The control mechanism 100 may be attached, mounted, affixed, or otherwise connected at the proximal end of barrel 104 such that at least a portion of the screw 132 resides inside barrel 104.

FIG. 7B shows an enlarged isometric view of the distal portion of the drug delivery syringe shown in FIG. 7A. Screw 132 may be connected to plunger seal 236 either directly or indirectly to drive the axial translation of the plunger seal 236. In the latter configuration, a plunger rod 234 may be utilized between screw 132 and plunger seal 236 to connect those components. The plunger rod 234 may be connected to the screw 132 at, for example, the screw connection aspect 136. In at least one embodiment, the screw connection aspect is connected to the plunger rod through a proximal opening 10 in the plunger rod such that the screw connection aspect sits within a proximal pocket in the plunger rod. Additionally or alternatively, this connection may be a snap-fit connection such as in the embodiment illustrated in FIGS. 7A and 7B, an interference-fit connection, or a number of other connection methods known in the industry.

In at least one embodiment, as is described further below with reference to FIGS. 9A-9D, the screw, screw connection aspect 136, and plunger rod are configured to be readily connectable after the drug chamber has been filled with a drug fluid and the plunger seal and plunger rod have been inserted into the proximal end of the barrel. Preferably, the connection between the screw 132 and the plunger seal 236, or screw 132 and plunger rod 234 when a plunger rod is employed, is such that the screw is permitted to axially rotate while the plunger rod and/or the plunger seal remain rotationally fixed. Accordingly, as the plunger 126 and screw 132 of the control mechanism 100 are axially rotated and translated, the motion is relayed to the plunger seal 236 which is also axially translated.

The control mechanism 100 additionally includes an automatic administration assembly 124 substantially as described above. When utilized within a pre-filled syringe, the control mechanism 100 including the automatic administration assembly 124 is generally attached to the barrel 240 after the drug chamber 238 of barrel 240 has been filled with a drug fluid. This is often desired so that the syringe 222 may be filled and assembled in standard pharmaceutical fill-finish process lines. Once the syringe 222 has been filled and assembled, the control mechanism 100 may be utilized by the user to identify and set the selected drug dose for delivery. The user may then inject the needle into the patient and actuate the actuator 186 to cause the plunger 126 and screw 132 to axially translate. Because of the function of the control mechanism and the pitch ratio, any measure of distal translation of the plunger 126 causes only an incremental measure of distal translation of the screw 132, permitting accurate dose delivery control by the user. Axial translation of the screw 132 causes axial translation of the plunger seal 236. This axial motion in the distal direction of the plunger seal 236 forces drug fluid out of drug chamber 238 of barrel 240, through the needle 254 of the barrel adapter assembly 250, for injection and delivery to the patient.

It will be appreciated that the control mechanism 100 of the present invention may likewise be utilized with safety syringes, such as retractable needle safety syringes (i.e., syringes which incorporate needle safety mechanisms). FIG. 8A shows an embodiment of the dose control mechanism 100 as a component of an exemplary retractable drug delivery syringe 300. As shown, the control mechanism 100 includes a plunger 126, a housing 128, an adapter 130, and a screw 132. Housing 128 may optionally include housing cover 144 at its proximal end, for example, to close the interior of the housing 128 off from the environment, to axially align plunger 126 within housing 128, and/or to prevent accidental removal of plunger 126. Housing 128 may further include a window 146, which may be an opening (e.g., an aperture) in the housing or a transmissive, translucent, and/or a component providing optical magnification. Plunger 126 may include one or more dose markings 148 on the external surface of the plunger 126. Housing 128 may have one or more reference or guide markings 150, such as at the window 146, with which to align or view plunger dose markings 148.

The control mechanism 100 further includes the automatic administration assembly 124 substantially as described in this disclosure. The control mechanism 100 may be attached, mounted, affixed, or otherwise connected the barrel 104 such that at least a portion of the screw 132 resides inside barrel 104.

Figure 8B:
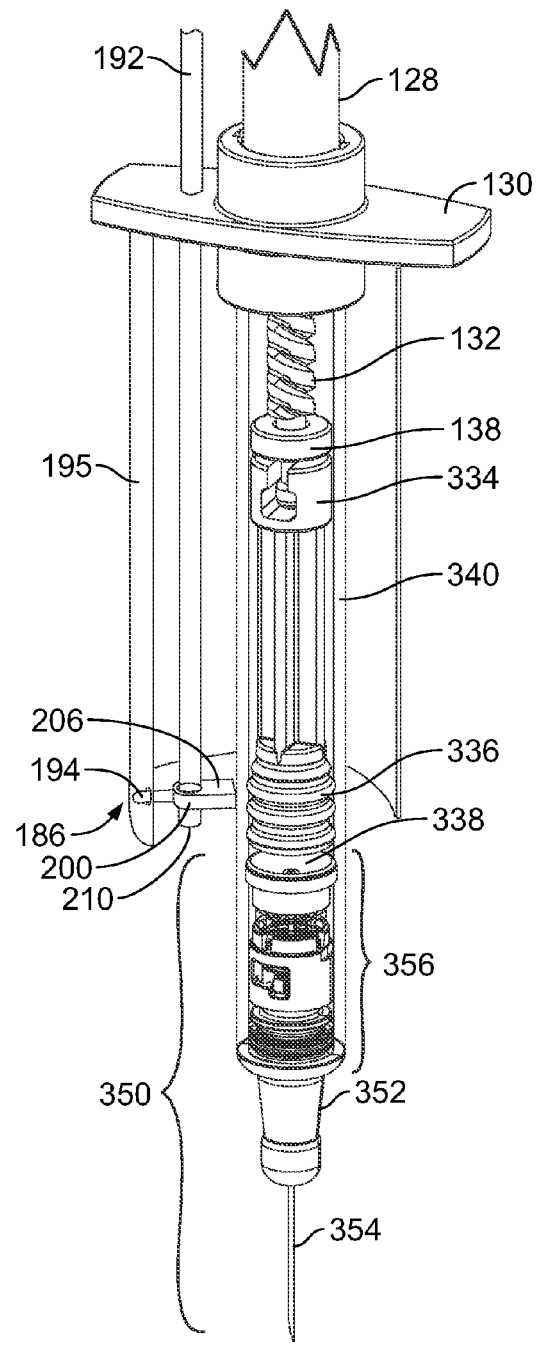
FIG. 8B shows an enlarged isometric view of the distal portion of the drug delivery syringe shown in FIG. 8A.

FIG. 8B shows an enlarged isometric view of the distal portion of the drug delivery syringe shown in FIG. 8A. Screw 132 may be connected to plunger seal 336 either directly or indirectly to drive the axial translation of the plunger seal 336. In the latter configuration, a plunger rod 334 may be utilized between screw 132 and plunger seal 336 to connect those components. The plunger rod 334 may be connected to the screw 132 at, for example, the screw connection aspect 136. The screw connection aspect may be connected to the plunger rod in the configuration described above with reference to FIGS. 6A and 6B, in the configuration described above with reference to FIGS. 7A and 7B, or any number of other connection methods known in the industry. Preferably, the connection between the screw 132 and the plunger seal 336, or screw 132 and plunger rod 334 when a plunger rod is employed, is such that the screw is permitted to axially rotate while the plunger rod and/or the plunger seal remain rotationally fixed. Accordingly, as the plunger 126 and screw 132 of the control mechanism 100 are axially rotated and translated, the motion is relayed to the plunger seal 336 which is also axially translated. The plunger 126 and screw 132 may function, substantially after the drug dose has been delivered, to initiate or engage a needle retraction or safety mechanism.

When utilized within a safety syringe, such as a retractable needle safety syringe, the plunger 126 of the control mechanism 100 is capable of engaging or initiating a needle safety mechanism. Suitably, the needle safety mechanism is facilitated by a biasing member such as a spring, elastic or other member capable of storing and releasing energy to facilitate needle retraction, needle sheathing, or any other method of protecting the user from accidental needle stick injuries. It will be appreciated that the safety syringe may comprise any needle safety mechanism, such as a needle retraction safety mechanism or needle sheathing safety mechanism, which is operable with the control mechanisms and syringes disclosed herein. By way of example, the needle safety mechanism may be a needle retraction safety mechanism as described in International Publication WO2006/119570, International Publication WO2006/108243, International Publication WO2009/003234, International Publication WO2011/075760, and/or U.S. patent application Ser. No. 13/693,915, although without limitation thereto. In at least one embodiment of the present invention, syringe 300 is a needle retraction safety syringe and incorporates the needle retraction safety mechanism 356 as disclosed in U.S. patent application Ser. No. 13/693,915.

Such a needle retraction safety mechanism 356 may be assembled to the syringe barrel 104, for example as part of the barrel adapter assembly 350, through the distal end of the barrel 104. The control mechanism 100 is generally attached to the barrel 340 after the drug chamber 338 of barrel 340 has been filled with a drug fluid. This is often desired so that the syringe 300 may be filled and assembled in standard pharmaceutical fill-finish process lines. Once the syringe 300 has been filled and assembled, the control mechanism 100 may be utilized by the user to identify and set drug dose for delivery. The user may then inject the needle into the patient for drug delivery. Subsequently, the actuator 186 may be actuated to cause the plunger 126 and screw 132 to axially translate. Because of the function of the control mechanism and the pitch ratio, any measure of distal translation of the plunger 126 causes only an incremental measure of distal translation of the screw 132, permitting accurate dose delivery control by the user. Axial translation of the screw 132 causes axial translation of the plunger seal 336. This axial motion in the distal direction of the plunger seal 336 forces drug fluid out of drug chamber 338 of barrel 340, through the needle 354 of the barrel adapter assembly 350, for injection and delivery to the patient. At the end of drug delivery, the plunger seal 336 is caused to contact a component of the needle retraction safety mechanism 356 to initiate the retraction mechanism thereby causing retraction of the needle 354 into the barrel 340 of syringe 300. The screw 132 and other components or the control mechanism 100 may be configured or adjusted to permit this additional range of axial 10 translation in the distal direction after the desired drug dose has been delivered. As the needle 354 is then retracted into the barrel 340 of syringe 300, components of the needle retraction safety mechanism 356 bear and push against plunger seal 336 in the proximal direction. As that retraction force is continued, the user may control the rate of needle retraction by controllably reducing the force they apply on the button 140 and/or plunger 126 as the screw 132 and plunger 126 move in the proximal direction. The needle retraction safety mechanism 356 therefore provides a number of additionally desirable features to the novel syringes of the present invention.

As would readily be appreciated by one having ordinary skill in the art, the barrel adapter assembly may be attached, mounted, affixed, or otherwise connected to the distal end of the barrel by a number of known methods. For example, a luer connection may be utilized to connect the barrel adapter assembly to the syringe barrel. Luer connection systems are a standard way of attaching syringes, catheters, hubbed needles, IV tubes, and the like to each other. Luer connections consist of conical/tubular male and female interlocking components slightly tapered to hold together better. Luer connections can either be a "luer slip", as shown in FIGS. 6A and 6B, which are luer connections with a simple pressure or twist fit; or luer connections be a "luer lock", as shown in FIGS. 7A and 7B, which can have an additional outer rim of threading allowing them to be more secure. Alternatively, the connection may be facilitated by a barrel adapter connection. By way of example, the barrel adapter connection may be as described in International Publication WO2011/137488 and/or U.S. patent application Ser. No. 13/693,915, although without limitation thereto. Luer connections, interference fit connections, barrel adapter connections, or any number of other known connections may be utilized to attach the barrel adapter assembly to the barrel while remaining within the breadth and scope of the present invention. Regardless of the type of barrel adapter assembly utilized, the barrel adapter assembly generally comprises of a barrel tip 116, 252, 352 and a needle 118, 254, 354, respectively. In some configurations, the barrel tip 116, 252, 352 may be a pre-formed aspect at the distal end of the barrel. Alternatively, the barrel tip 116, 252, 352 may be a separate component that is attached at the distal end of the barrel. The needle 118, 254, 354 may be any type of fluid conduit including, for example, a flexible cannula or a rigid needle, and may be made of any number of materials, including stainless steel. The type of connections described herein can be utilized regardless of the type of syringe with which they are shown. For clarity, the luer slip connection shown with the fill-at-time-of-use syringe in FIGS. 6A and 6B may be utilized with the pre-filled syringe in FIGS. 7A and 7B, or any other type of connection may be used with any other type of syringe described herein.

As noted above, the dose control mechanism 100 of each of syringes 220, 222, 300, further includes automatic administration assembly 124 substantially as described in this disclosure. The automatic administration assembly 124 includes an administration mechanism 182, a locking mechanism 184, and an actuator 186. By way of the automatic administration assembly 124, the user may preselect the volume of drug to administer, then actuate the dose control mechanism 100 to deliver the drug without the user physically depressing the plunger 126. Thus, in use of each of the syringes 220, 222, 300, the user first selects the desired volume of drug to be delivered using the selection dial 190. The rotation of the selection dial 190 energizes the biasing member 188, while the locking pin 192 held between the selection dial 190 and the abutment surface 206 of the locking arm 200, that is, the locking mechanism 184, locks the selection dial 190 with the biasing member 188 in the energized position. Upon a desired placement of the needle 118, the dispense button 194 is depressed to actuate dispensing of the drug. With the selection dial 190 no longer held in position, the biasing member 188 deenergizes, imparting rotation to the plunger 126. As explained in detail above, as the plunger 126 rotates by way of its course pitch thread 154 along the course pitch guide 156 of the housing 128, the rotationally keyed screw 132 rotates along its fine pitch thread 158 engaged with the fine pitch nut 160 of the adapter 130. The translational, axial movement of the screw 132 is transmitted to the plunger seal 114, here, by way of plunger rod 170 to dispense the drug.

It will be appreciated from the foregoing that the novel dose control mechanisms and syringes disclosed herein provide an efficient and easily operated system for the accurate dose setting and delivery of drug treatments. Such devices are safe and easy to use, and are aesthetically and ergonomically appealing for clinical practitioners. The embodiments of the present invention overcome the challenges faced with the use of conventional syringes for the dosing and delivery of low-volume treatments by utilizing novel dose control mechanisms. The novel dose control mechanisms permit the user to accurately read and dose the desired volume of drug treatment for delivery to the patient.

Assembly and/or manufacturing of control mechanism 100, syringe 102, syringe 220, 222, 300 or syringe 400, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. For example, a glue or adhesive may be utilized to connect the distal end of the housing 128 to the proximal end of adapter 130. Similarly, a glue or adhesive may be utilized to connect the distal end of adapter 130 to 15 the proximal end of the barrel. Additionally, known siliconization fluids and processes may be employed during the manufacture of the novel components and devices. Furthermore, known sterilization processes may be employed at one or more of the manufacturing or assembly stages to ensure the sterility of the final product.

In one embodiment, a method of assembling the control mechanism includes the steps of:

(i) threading a fine pitch screw at least partially through a fine pitch nut of an adapter;

(ii) inserting a plunger through a selection dial and a biasing member, (iii) threading the plunger, the plunger having a coarse pitch screw on its outer surface and an annular space within its inner surface, at least partially through an interior axial pass-through of a housing, wherein the housing interior has a corresponding coarse pitch guide;

(iv) inserting at least a proximal portion of the screw into the annular space of the plunger through a distal portion of the plunger;

(v) attaching the outer distal portion of the housing to a proximal aspect of the adapter;

(vi) disposing a locking pin between the selection dial and a locking arm; and (vii) providing an actuator operatively connected to the locking arm.

The control mechanism may be utilized as a component of a syringe. In one embodiment, the method of manufacturing a syringe comprising a control mechanism includes the steps of:

(i) mounting a barrel adapter assembly to a distal end of a syringe barrel;

(ii) mounting a plunger seal through a proximal end of the syringe barrel; and (iii) mounting a control mechanism to the proximal end of the syringe barrel, wherein a portion of the control mechanism rests in contact with the plunger seal.

The method of manufacturing a syringe may further comprise, before the step of (ii) mounting a plunger seal through a proximal end of the syringe barrel, the step of: filling the barrel at least partially with a fluid substance. Step (iii) may further require the step of connecting a screw connection aspect of a screw of the control mechanism directly to the plunger or indirectly through a plunger rod which is connected at the proximal end of the plunger seal. The connection between the plunger rod and the plunger seal may be any number of connections including, but not limited to, screw-type connection, snap-fit connections, interference connections, capture connections, and the like. In at least one embodiment, the screw connection aspect is connected to the plunger rod through a radial opening or a proximal opening in the plunger rod such that the screw connection aspect sits within a proximal pocket in the plunger rod. Additionally or alternatively, this connection may be a snap-fit connection, an interference-fit connection, or a number of other connection methods known in the industry. Preferably, the connection between the screw and the plunger seal, or between the screw and plunger rod when a plunger rod is employed, is such that the screw is permitted to axially rotate while the plunger rod and/or the plunger seal remain rotationally fixed.

Figures 9A, 9B:
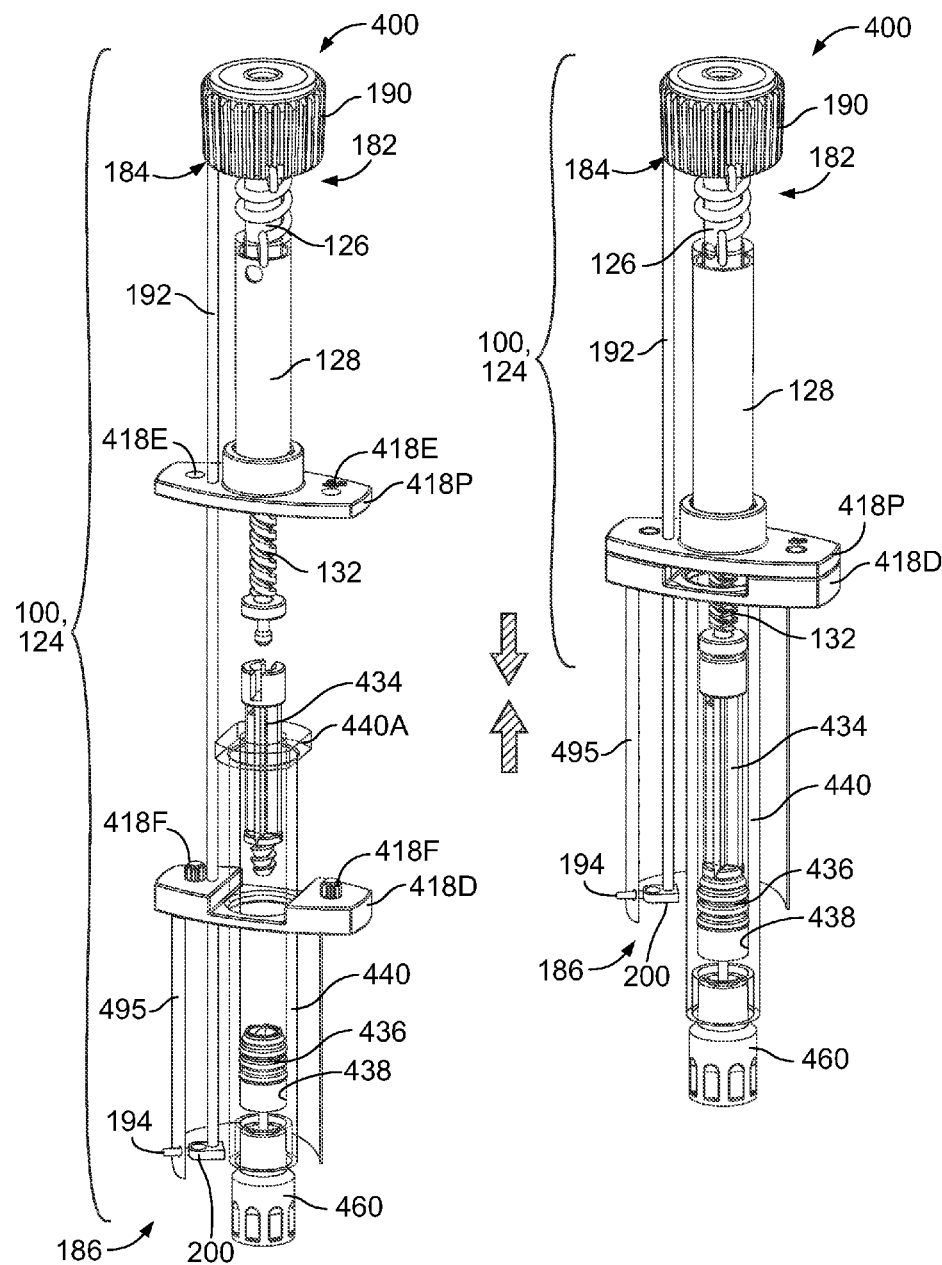
FIG. 9A shows an isometric view of an initial assembly stage of a pre-filled drug delivery syringe that may incorporate an automatic administration assembly according to at least one embodiment of the present invention.
FIG. 9B shows an isometric view of the automatic drug delivery syringe shown in FIG. 9A after it has been assembled.

One preferred method of manufacturing a syringe having a dose control mechanism, according to one embodiment of the present invention, is described herein with reference to FIGS. 9A-9D. FIG. 9A shows a pre-filled syringe, such as that described with reference to FIGS. 7A-7B above, except that the adapter is a two-component adapter having a proximal adapter portion 418P and a distal adapter portion 418D. An automation housing 495 may be formed with or secured to the distal adapter portion 418D, as illustrated. Alternately, such an automation housing 495 may extend distally from the proximal adapter portion 418P and ultimately be assembled around the distal adapter portion 418D (not illustrated). Proximal adapter portion 418P has one or more connection ports 418E and distal adapter portion 418D has corresponding connection prongs 418F. When forced together, connection prongs 418F and corresponding connection ports 418E merge, mate, or otherwise connect to unite the two portions of the adapter 418P, 418D.

Initially, a cap 460 may be connected to the distal end of barrel 440 of syringe 400. The distal adapter portion 418D may be slidably mounted to the exterior of the barrel 440. The interior of the barrel 440, i.e. the drug chamber 438, may be filled with a drug fluid or substance through the open proximal end of the barrel. The plunger seal 436 may be mounted into the barrel through the proximal end such that is in contact with the fluid. The optional plunger rod 434 may be connected to the plunger seal 436 prior to, or after, insertion of the plunger seal 436 into the barrel 440. These steps may be performed in a sterile environment to maintain the container integrity and sterility of the drug treatment.

The remainder of the syringe may then be assembled in a non-sterile or sterile environment. The screw 132, as a component of the control mechanism 100, may then be connected to the plunger seal 436 or to the plunger rod 434 when a plunger rod 434 is employed. The distal adapter portion 418D may then be slid in the proximal direction along the exterior of the barrel to connect to the proximal adapter portion 418P as described above. The locking pin 192 may be slid through an aperture in the distal adapter portion 418D, and brought into contact with the locking arm 200. The connection between the distal adapter portion 418D and the proximal adapter portion 418P may capture a barrel flange 440A aspect of the barrel 440 in order to retain the control mechanism 100 at the proximal end of the barrel 440.

Figures 9C, 9D:
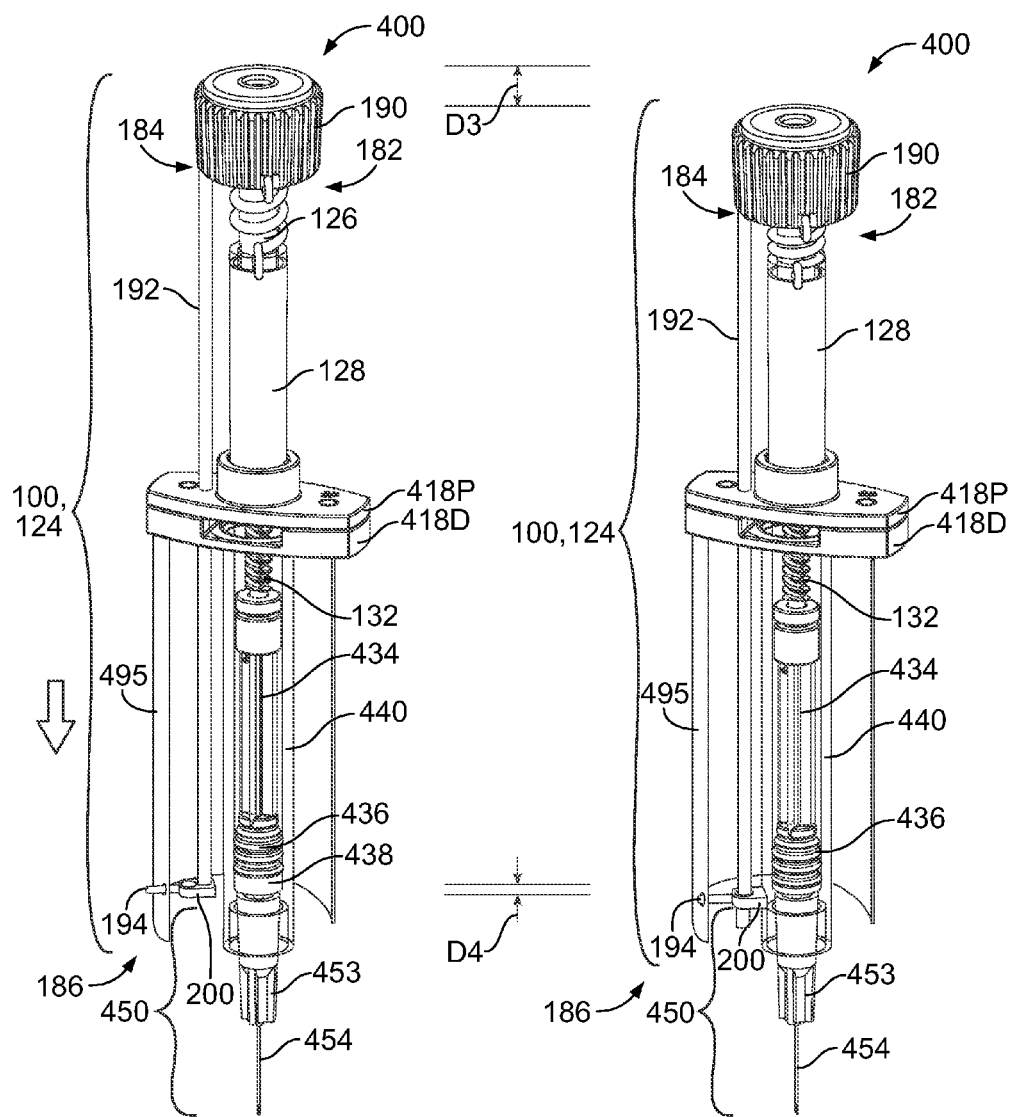
FIG. 9C shows an isometric view of the automatic drug delivery syringe shown in FIG. 9A in a ready-to-inject stage of operation.
FIG. 9D shows an isometric view of the automatic drug delivery syringe shown in FIG. 9A in an end-of-dose stage of operation.

Various glues or adhesives may be utilized to ensure that such components and connections are retained in position during assembly, filling, manufacturing, transportation, storage, and operation of the novel devices of the present invention. The final assembly of the syringe, such as in the pre-filled syringe 400, may appear as shown in FIG. 9B, and with the automatic administration assembly 124 assembled thereto as illustrated in FIG. 9C. This type of pre-filled syringe may be utilized when, for example, a syringe is to be filled with a standard amount of drug fluid by a pharmaceutical company or contract drug filler, when the drug dose is variably selectable by the user, when the needle length is variably selectable by the user, or in a number of other situations. FIG. 9C also shows the pre-filled syringe with a selectable needle that is attached via a luer lock connection, as described above. In such a scenario, the syringe may be held such that the distal end of the syringe is pointed upwards. The cap 460 (shown in FIG. 9B) may be removed and replaced by a barrel adapter assembly 450. The barrel adapter assembly 450 includes a barrel tip 453 and needle 454 which may be selected by the user and attached to the pre-filled syringe just prior to use. The drug dose may be identified and selected by the user, as described above. Comparison of the pre-filled syringe 400 in FIGS. 9C and 9D clarifies the differences in the pre-filled syringe just prior to, and after, injection and delivery of the drug dose to the patient. Because of the pitch ratio between the plunger 126 and the screw 132, screw 132 is caused to axially translated in the distal direction only incrementally or to a lesser distance when plunger 126 is depressed or axially translated in the distal direction (i.e., in the direction of solid arrow in FIGS. 9C and 9D). This difference in axial translation distance between plunger 126 and screw 132 is visible by comparing distances D3 and D4 in FIGS. 9C and 9D. D3 is the distance that plunger 126 axially translates while D4 is the fractional distance that screw 132 axially translates.

Accordingly, the novel embodiments of the present invention provide dose control mechanisms, which allow for the accurate dosing and delivery of drug treatments, and drug delivery syringes which incorporate such control mechanisms. Such novel devices permit the identification and control of the dosage amount, permit the syringe to be "primed" (i.e., evacuated of air bubbles) prior to drug delivery, and ensure the accurate delivery of microliter volume dosages, all within a device size that is similar to commonly used conventional syringes available in the marketplace. Such novel devices are safe and easy to use, and are aesthetically and ergonomically appealing for clinical practitioners. The novel devices of the present invention provide these desirable features without any of the problems associated with known prior art devices.

Figure 10:
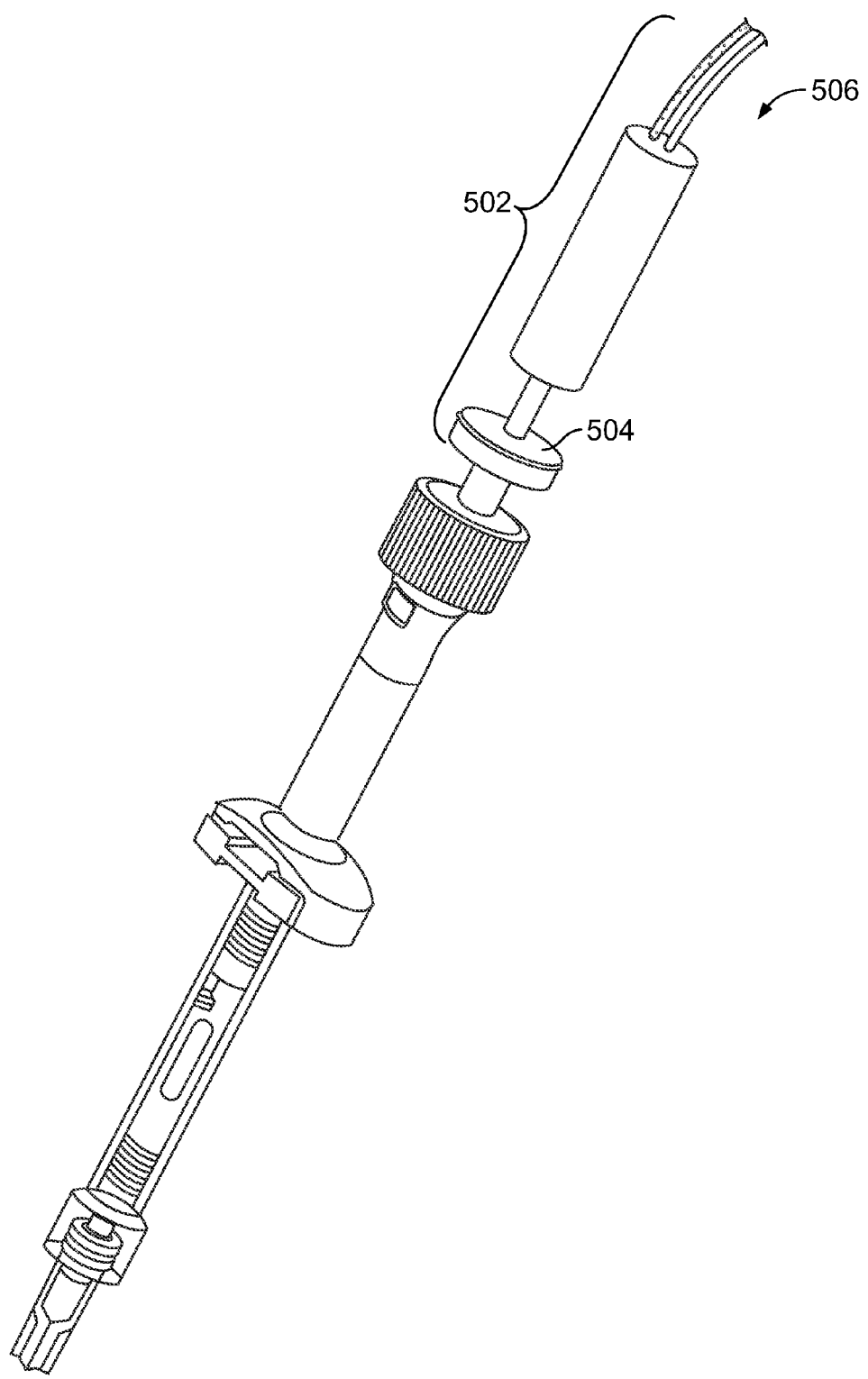
FIG. 10 shows an isometric view of an automatic drug delivery syringe, according to at least a sixth embodiment of the present invention.

A number of known filling processes and equipment may be utilized to achieve the filling steps of the syringe manufacturing process. The barrel assembly, needle, plunger seal, plunger rod, and other components described in these manufacturing and assembly processes may be as described above or may be a number of similar components which achieve the same functionality as these components. Throughout the specification, the aim has been to describe the preferred embodiments of the invention without limiting the invention to any one embodiment or specific collection of features. Various changes and modifications may be made to the embodiments described and illustrated without departing from the present invention. The disclosure of each patent and scientific document, computer program and algorithm referred to in this specification is incorporated by reference in its entirety.

In an alternative preferred embodiment, as shown in FIG. 10, the administration mechanism may include one or more electrical, mechanical, or electromechanical components 502 that, for example, act on the plunger, causing it to axially translate and axially rotate, as described further herein. As with the embodiments described above, torque may be transferred from the plunger to the fine pitch screw by way of the keyed interface, and from the fine pitch screw rotating as a result of engagement with the fine pitch nut to provide translational movement to the plunger seal, by way of a plunger 10 rod, if provided. The plunger rod preferably only axially translates, i.e. the plunger rod does not axially rotate, due to the slip fit with the screw. The plunger seal is caused to translate as it is connected or adjacent to the plunger rod, thereby delivering a drug or therapy to a user through a needle or cannula.

When an electrical, mechanical, or electromechanical arrangement 502 is utilized as the administration mechanism, the torque of such component is utilized to translate the plunger seal for drug delivery. In a particular embodiment, an electromechanical biasing member, such as a motor 504, is employed to cause axial translation and axial rotation of the plunger. In such an embodiment, the administration mechanism may be coupled with the locking mechanism. That is, lack of actuation of a motor necessarily provides a locking mechanism, maintaining the plunger in a given position. The motor, such as a stepper motor, may be controlled by a myriad of actuators 506, mechanisms or methodologies. For example, the motor, biasing member, and/or plunger may be controlled by a foot-operated actuator, a voice-activated actuator, or other such control or actuation mechanism. In at least one particular embodiment, the biasing member is controlled by a foot-operated actuation mechanism. In another particular embodiment, the biasing member is controlled by a voice-activated actuation mechanism. For example, the biasing member may be configured to deliver a predetermined volume of dose each time a user issues a command such as the word "dose." In a preferred embodiment, these components may be configured to operate with the dose control mechanisms as described in International Publication WO2013/086167, although without limitation thereto.

In summary, in accordance with the invention, various embodiments of syringes include control mechanisms that include an automatic administration assembly having keyed members having respective thread pitches with a pitch ratio that determines the relative translational movement of a plunger seal, and an automatic administration assembly including an administration mechanism, a locking mechanism, and an activator. The administration mechanism may be, for example, a biasing member such as a spring, for example, a compression spring and/or a torsional spring. The administration mechanism, locking mechanism, and activator are configured such that actuation of the activator by the user manipulates the locking mechanism to permit the administration mechanism, such as a biasing member, to move from an initial energized state to a lower energy or deenergized state. In the case of an administration mechanism such as a motor, the activator permits movement of the administration mechanism from a locked state to administer the drug. In one embodiment, when the activation button is depressed, a locking pin of the locking mechanism is manipulated to release the plunger of the syringe. The biasing member is then permitted to act on the plunger, causing it to axially translate and axially rotate. Torque may be transferred from the plunger to the coarse pitch screw by way of a keyed interface, and from the fine pitch screw to the plunger seal as a result of the engagement of the fine pitch screw with the fine pitch nut, optionally by transferring force to the plunger seal by way of a plunger rod. The plunger rod preferably only axially translates, i.e. the plunger rod does not axially rotate, due to the slip fit with the screw. The plunger seal is caused to translate as it is connected or adjacent to the plunger rod, thereby delivering a drug or therapy to a user through a needle or cannula. When a torsional spring, or a torsional compression spring, is utilized as the biasing member, the torque of the spring is thus utilized to translate the plunger seal for drug delivery. These components may be configured to operate with the dose control mechanisms of essentially any design, either as an add-on or by being integrally formed with the syringe.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

We claim:

1. An automated dose control mechanism for a syringe having a barrel and a plunger seal, the dose control mechanism comprising:
   a plunger assembly adapted to be connected to the syringe to provide movement to the plunger seal, the plunger assembly including a housing and a plunger rotatable relative to the housing; and
   an automatic administration assembly including
   an administration mechanism adapted and disposed to provide movement to the plunger assembly, the administration mechanism including a selection dial and a biasing member, the biasing member having an anchor end coupled to the housing and a rotatably mounted end coupled at least one of the selection dial and the plunger, the selection dial configured to rotate the plunger to set a dose volume and rotate the rotatably mounted end of the biasing member, a locking mechanism configured to engage the selection dial and adapted to be selectively disposed in an engaged position and a disengaged position, wherein the engaged position prevents the administration mechanism from providing movement to the plunger assembly, and the disengaged position does not prevent the administration mechanism from providing movement to the plunger assembly, and an actuator, the actuator disposed to selectively disengage the locking mechanism whereby the administration mechanism provides movement to the plunger assembly when the locking mechanism is disengaged without requiring further actuation.

2. The automated dose control mechanism of claim 1 wherein the biasing member is a spring.

3. The automated dose control mechanism of claim 1 wherein movement of the selection dial energizes the biasing member.

4. The automated dose control mechanism of claim 1 wherein the locking mechanism includes a locking pin.

5. The automated dose control mechanism of claim 4 wherein the locking mechanism further includes an abutment surface that maintains the locking pin in an engaged position.

6. The automated dose control mechanism of claim 1 wherein the actuator includes a dispense button.

7. The automated dose control mechanism of claim 5 wherein the actuator includes a dispense button adapted to move the abutment surface from a position engaging the locking pin to a position no longer engaging the locking pin.

8. The automated dose control mechanism of claim 1 wherein the spring is a torsion spring.

9. A syringe including the automated dose control mechanism of claim 1.

10. The syringe of claim 9 wherein the syringe is a prefilled syringe.

11. The syringe of claim 9 wherein the syringe is a retractable needle syringe.

* * * * *